United States Patent [19]
Lau et al.

[11] Patent Number: 5,976,800
[45] Date of Patent: Nov. 2, 1999

[54] ENHANCEMENT OF CANCER CELL DEATH

[75] Inventors: Allan S. Lau; Michael C. Yeung, both of San Francisco, Calif.

[73] Assignee: The Regents of the University of California, Oakland, Calif.

[21] Appl. No.: 08/883,698

[22] Filed: Jun. 27, 1997

Related U.S. Application Data

[60] Provisional application No. 60/020,849, Jun. 28, 1996.

[51] Int. Cl.[6] ................................ C12Q 1/68; C12Q 1/48
[52] U.S. Cl. .................................................. 435/6; 435/15
[58] Field of Search ............................................ 435/6, 15

[56] References Cited

U.S. PATENT DOCUMENTS 5,670,330   9/1997   Sonenberg et al. ........................ 435/15

*Primary Examiner*—Ponnathapura Achutamurthy
*Assistant Examiner*—M. Monshipouri
*Attorney, Agent, or Firm*—Cooley Godward LLP

[57] ABSTRACT

The invention provides for methods and compositions based on the expression of cellular levels of double-stranded RNA dependent kinase (PKR), an interferon-regulated gene, is used to enhance cancer cell death. The PKR gene is encoded by vectors, optionally containing specific promoters that are activated only in specific target cells. Cells producing PKR are treated with non-toxic, low doses of apoptosis-inducing agents, such as TNF-α or poly I:C, leading to programmed cell death without the use of conventional chemotherapeutic agents. Designing of recombinant viral vectors for gene therapy based on these expression systems for the treatment of human hepatitis B and C viruses, human papilloma virus, and other cancers and viral diseases is also taught.

34 Claims, 16 Drawing Sheets

C.

F.

B.

E.

A.

D.

Viability of U937 Cells post TNF-α Treatment

Viability of U937 cells Treated With Increasing Amounts of TNF-α

Viability of U937 Cells Treated with TNF-α and Poly I:C

Viability of HeLa Cells After TNF-α Treatment

Viability of HeLa Cells Treated with Poly I:C

Viability of HeLa Cells Treated with TNF-α and Poly I:C

ENHANCEMENT OF CANCER CELL DEATH

CROSS-REFERENCE TO RELATED APPLICATION

This application claims the benefit of U.S. Provisional Application Ser. No. 60/020,849, filed Jun. 28, 1996.

INTRODUCTION

1. Technical Field

The invention relates to methods and compositions for cancer treatment using vectors expressing serine/threonine protein kinases that are activated by double-stranded RNA to enhance the sensitivity of neoplastic cells to immunomodulators and chemotherapeutic agents.

2. Background

Cancer therapy, especially a type of therapy that can be applied to different types of cancers, remains a goal of medicine. A number of different treatments have been used with varying degrees of success. In general, treatment of cancer includes surgical resection, x-ray irradiation, radioisotope treatment, conventional chemotherapy, or specific combinations of these types of treatments. These methods have inherent limitations, however. For example, surgical resection, while targeted at grossly identifiable tumor mass, is limited in scope and cannot eliminate microscopic, metastatic tumor cells. Irradiation and radioisotope therapy, by contrast, are potent and effective for microscopic cancer cells, but can induce extensive damage of normal tissues which may result in permanent fibrosis and scarring. Similarly, conventional chemotherapy often causes tumor cell death by directly intoxicating both normal and malignant cells. The non-specific nature of the cytotoxicity resulting from these treatments poses significant problems for the patient, including massive tissue necrosis, potential kidney damage due to renal overload by metabolic waste such as uric acids, bone marrow failure, and gastrointestinal mucosal sloughing and bleeding.

One of the major obstacles in this area is to develop a treatment regime that works despite the multiple pathways that contribute to cancer cell and tumor growth. A number of genes have been implicated in the transformation of normal cells to neoplastic cells, and cancer cell growth and proliferation. Often, multi-activation of cancer cells thwarts effective treatment.

Consequently, there is a great need for cancer treatments that can be used to combat different types of cancers and can arrest cancer growth despite the multiply-activated oncogenic pathways.

SUMMARY OF THE INVENTION

The present invention provides a method of enhancing cancer cell death by manipulating the expression of PKR (double-stranded RNA dependent protein kinase), based on the discovery that expression, particularly over-expression, of PKR renders cancer cells more prone to develop apoptosis, i.e. programmed cell death.

Additionally, the method of the present invention comprises contacting the PKR expressing cancer cells to low dosages of immunomodulators including poly I:C, TNF-α, or chemotherapeutic agents. Apoptosis of cancer cells which over-express the PKR protein is further enhanced by addition of these low dose secondary agents. One particular advantage of the invention is to reduce detrimental side effects of high doses of agents to treat cancer, such as immunomodulators or chemotherapeutics. For example, the invention can reduce TNF-α's toxicity at high levels in vivo, which contribute to metabolic disturbances, wasting, and suppression of hemopoiesis. Furthermore, the present invention is useful because cancer cells are more sensitive to low levels of "ambient" TNF-α in the vicinity of tumor cells in a mammal due to the natural anti-tumor response. Therefore, the addition of secondary agents is not required in all instances of enhancing cancer cell death, according to the present invention.

Another aspect of this invention comprises utilizing a tumor-related virus as a vehicle for the delivery of the PKR gene as a means of gene therapy. Specifically, viral vectors encoding PKR driven by viral or cell-specific promoters can be used as vectors for gene therapy for cancer cells or for specific virus-infected cells, e.g., hepatocarcinoma and cervical carcinoma cells. The use of specific viral vectors for the particular virus-related cancer along with the viral vector-encoding PKR driven by the particular virus promoter, according to the method of the present invention, provides advantages including the following:

(a) killing of the cancer cells in an organized and timed fashion, i.e., programmed cell death by PKR, an important signaling molecule which achieves cell death in a manner similar to natural immune surveillance;

(b) targeting of the therapy to the proper cells through tissue-specific viral vectors for the virus-related cancer cells;

(c) targeting of the therapy to the proper cells through the specific activation of PKR expression by viral transactivators that are known to be present in the virus-related cancer cells;

(d) eliminating the use of excessive cytotoxic chemotherapy; and (e) controlling the degree of tumor lysis by adjusting the concentration of the secondary agents that further enhance apoptosis to avoid sudden, massive tumor lysis which, in turn, minimizes necrotic cell death and inflammatory response.

The present invention is based, in part, on the recognition that TNF-α treatment results in the activation of several serine/threonine protein kinases, that TNF-α and PKR mobilize NF-κB, and that PKR is a serine/threonine protein kinase and is growth-inhibiting. The discovery is that PKR induces insidious onset of apoptosis in cancer cells, especially when followed by treatment of the cells with non-toxic doses of TNF-α or poly I:C. The present invention is useful in combating different types of cancers, despite potentially different oncogenic pathways.

BRIEF DESCRIPTION OF THE DRAWINGS

FIGS. 5A1–5D show promonocytic U937 cell viability after TNF-α and poly I:C treatments. Cells were treated with TNF-α or poly I:C for the indicated time intervals at indicated concentrations and were diluted five-fold with 0.4% trypan blue in PBS for viable cell counts, which are expressed as percentages of viable cell counts of untreated cells (U9K-C). Results are representative of experiments done over three times.

FIG. 5A1 shows U9K-C, U9K-S and U9K-A cells that were treated with either 0.5 ng/mL (10 units) or 5 ng/mL (100 units) of TNF-α (1 ng=20 units) for 18 hours.

FIG. 5A2 shows U9K-C, U9K-S and U9K-A cells that were treated with 0.1 μg/mL poly I:C for 18 hours.

FIG. 5D shows viability of U937 cells treated with TNF and poly I:C. U9K-S and U9K-C cells were treated with TNF-α (0.5 ng/ml) and poly I:C (0.1 μg/ml) for 24 hours.

FIG. 9A shows HeK-C, HeK-S, and HeK-A cells that were treated with 0.5 (open bars) or 5.0 (dotted bars) ng/mL of TNF-α (1 ng=20 units) for 18 hours. HeK-C represents HeLa cells transfected by the parental plasmid without PKR inserts. HeK-S represents HeLa cells transfected with the plasmid containing PKR insert in the sense orientation; HeK-A represents HeLa cells transfected with the plasmid containing PKR insert in the antisense orientation.

FIG. 9B shows HeK-C and HeK-S cells that were treated with indicated concentrations of poly I:C at 0.1, 0.5, and 1.0 μg/ml for 18 hours.

FIG. 9C shows cells that were treated with TNF (0.5 ng/ml) and poly I:C (0.1 μg/ml) over a time course of 14 days.

DESCRIPTION OF SPECIFIC EMBODIMENTS

Abbreviations

Figure 1:
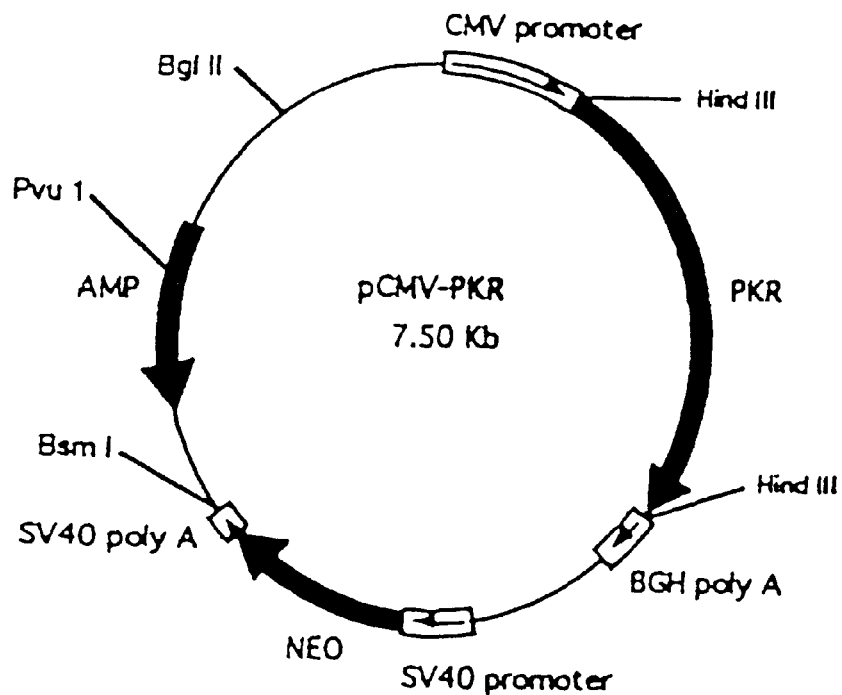
FIG. 1 presents a diagram of an expression vector, pCMV-PKR, showing the human PKR cDNA in the sense orientation driven by the promoter sequence from the immediate early gene of human cytomegalovirus.

IFN, interferon; dsRNA, double-stranded RNA; TNF, tumor necrosis factor; PKR, double-stranded RNA dependent protein kinase; RT-PCR, reverse transcription-polymerase chain reaction; GAPDH, glyceraldehyde-3-phosphate dehydrogenase; ICE, interleukin-1β converting enzyme; poly I:C, polyriboinosinic:polyribocytodylic acid; NF-κB, nuclear factor κB; IκB, inhibitor κB; TGF, transforming growth factor, PDGF, platelet derived growth factor; EGF, epidermal growth factor.

Introduction

The present invention recognizes that human cancer cells expressing PKR, compared to non-neoplastic cells or noncancer cells which normally do not express PKR, are highly sensitive to TNF or poly I:C or a combination thereof. The present invention also recognizes for the first time that cell apoptosis can be selectively induced in cancer cells expressing PKR by contacting the cells with TNF or poly I:C or a combination thereof. The present invention, thus, permits preferentially induction of apoptosis, in cancer cells compared to normal cells.

Prior to the invention described herein it was not known (1) how TNF induces apoptosis; (2) whether TNF induces apoptosis through PKR; (3) how poly I:C induces apoptosis; (4) whether poly I:C induces apoptosis through PKR; (5) whether PKR expression would increase the sensitivity of cancer cells, compared to non-neoplastic cells, to either TNF or poly I:C; (6) whether PKR expression would simultaneously increase the sensitivity of cancer cells, compared to non-neoplastic cells, to a combination of TNF and poly I:C; (7) whether PKR could selectively induce apoptosis of neoplastic cells, compared to non-neoplastic cells; and (8) whether PKR renders cancer cells more sensitive to immunomodulators and/or chemotherapeutic agents for cancer therapy. The present invention now recognizes that PKR can be used to promote the inhibition of cancer cell proliferation or cancer cell apoptosis using TNF or poly I:C or a combination thereof.

As a non-limiting introduction to the breadth of the invention, the invention provides several categories of useful methods, compounds and compositions:

1) methods directed to treating cancer that includes delivery and expression of a PKR gene to the tumor or cancer cells using a viral vector or plasmid encoding the PKR gene and usually driven by a tissue-specific promoter,
2) methods directed to selectively killing cancer cells expressing PKR using TNF or poly I:C or a combination thereof,
3) methods directed to inducing tumor regression of tumors expressing PKR using TNF or poly I:C or a combination thereof,
4) methods directed to preventing tumor growth of tumors expressing PKR using TNF or poly I:C or a combination thereof,
5) a PKR-expression system that is useful for treating cancer,
6) a method and assay system for screening candidate chemotherapeutic compounds,
7) a method to render cancer cells more susceptible or sensitive to immunomodulators and/or chemotherapeutic agents,
8) a method combining the use of chemotherapy with PKR-mediated gene therapy, and
9) a method and screening system using PKR(+) cells to provide a sensitive cell line to evaluate efficacy of apoptosis-inhibiting agents.

The invention is made possible, in part, by the discovery that expression of the PKR gene in cancer cells causes apoptosis, as evidenced by light and electron microscope observations, analysis of DNA fragments, and determination of RNA levels, and that the apoptosis of cancer cells is enhanced by the addition of TNF or poly I:C to the cancer cells. IFN, TGFβ, PDGF, EGF or any other cytokine and/or immunomodulators may also be used to cause PKR expression.

METHODS OF TREATMENT AND PKR EXPRESSION SYSTEMS

Cell death is a normal and important physiological process in most, if not all, multicellular organisms. The present invention advantageously utilizes cell death processes to selectively kill cancer cells or preferentially arrest cancer cell proliferation compared to non-neoplastic cells. Most cells in metazoan animals can activate a self-destruct, or cell-intrinsic suicide, process to implement apoptosis or programmed cell death (reviewed in Orrenius, S., *Intern Med.*, 237:529–36 (1995); Stellar, H., *Science*, 267:1445–1462 (1995); Vaux, D., *Proc Natl Acad Sci*, 90:786–789 (1993). There are many advantages for these organisms to benefit from cell death, both during development and for homeostasis. The present invention, however, can utilize this endogenous system to directly promote cell death.

As described herein for different embodiments of the invention, the programmed cell death process is often associated with characteristic morphological and biochemical changes (Hunter, T., *Curr Opin Gen Dev*, 3:1–# (1993)). Once committed to apoptosis, cells undergo new rounds of protein synthesis and various morphological and physiological changes including cell shrinkage, cytoplasmic condensation, nuclear chromatin condensation, membrane blebbing, and eventually DNA degradation into the characteristic oligonucleosomal ladder comprised of multiples of 200 base pairs (Levine, A., *Annu Rev Biochem*, 62:623–# (1993)). These changes can be followed as known in the art or described herein. The dying cell eventually fragments into membrane-bound apoptotic bodies that are rapidly phagocytosed and digested by macrophages or by neighboring cells. In this way, dead cells are removed in an orderly manner without any leakage of their noxious and potentially proinflammatory contents. By contrast, during necrosis, a pathological form of cell death that results from overwhelming cell injury, cells swell and lyse rapidly, thereby releasing cytoplasmic contents which invariably trigger an inflammatory response. The present invention can thus offer the advantage of directing the killing of cancer cells while minimizing side-effects due to inflammation.

It is commonly believed that apoptosis naturally occurs during growth, development, and homeostasis of metazoans. During fetal growth, apoptosis plays a crucial role in sculpting the development of the fetal animal (Cohen, J. et al., *Annu Rev Immunol* 10:267–# (1992)), precisely regulating cell number in tissues, and controlling the formation of organs (Nagata, S. et al., *Immunol Today* 16:39–# (1995)). In developing and adult organisms, cell death plays an important role for homeostasis. It serves as a defense mechanism to remove unwanted and potentially dangerous cells, including virus-infected cells, self-reactive lymphocytes in autoimmune diseases, or malignant cells (Oehm, A. et al., *J Biol Chem*, 267:10709–# (1992); Yonehara, S. et al., *J Exp Med*, 169:1747–# (1989); Vaux, D., *Proc Natl Acad Sci* 90:786–7890. (1993)). Apoptosis may also be used to minimize the risk of developing potentially cancerous cells in tissues frequently exposed to mutagenic chemicals, carcinogens, or UV radiation. For example, epithelial cells in the gut die by physiological means (Duncan, A. et al., *Cancer Lett*, 23:307–311 (1984)). In the skin, physiological cell death is used to remove UV-exposed epidermal cells relatively rapidly, rather than by prolonged, passive shedding which may have a risk for malignant transformation (Young, A., *Photo-dermatology*, 4:127–134(1987)). As a further protection against malignancy, TNF can trigger the apoptotic death of transformed host cells (Heller, R., *Cell*, 70:47–56 (1992)).

In view of the potent effects of apoptosis on growth, development, and homeostasis, it is not surprising to find that the initiation of apoptosis is tightly regulated, especially in normal cells. Diverse exogenous or endogenous signals regulate the cellular decision to maintain life or to proceed to apoptosis in metazoan cells. These signals regulate: (i) cellular origin, lineage and degree of differentiation, (ii) cellular damage inflicted by the extracellular or intracellular environment including radiation, chemical carcinogens, metabolic oxidants and viral infections, (iii) cell-to-cell interaction, and (iv) interaction of the cell with hormones and cytokines, such as TNF and IFN. These diverse signals may either suppress or promote the activation of apoptosis; and a specific signal may have opposing effects on different cell types.

The present invention recognizes that apoptosis is tightly regulated and that in normal cells, as opposed to cancer cells, the PKR gene is not expressed at sufficient levels to participate in the promotion of apoptosis. The present invention, instead, promotes selective killing of cancer cells that express PKR. Such cancer cells are more sensitive to poly I:C, tumoricidal agents including TNF, as well as other chemotherapeutic agents.

The present invention focuses on cancer cell expression of PKR, which is a serine/threonine protein kinase inducible by IFNs and activated by dsRNA following viral infection (Galabru, J. et al., *J. Biol. Chem.*, 262:15538–15544 (1987); Meurs, E. et al., *Cell*, 62:379–390 (1990)). PKR is also a growth-suppressor gene. By phosphorylating the eukaryotic translation initiation factor-2 (eIF-2), PKR inhibits further protein synthesis and thus contributes to the host viral defense (Dever, T. et al., *Proc Natl Acad Sci USA*, 90 (10):4616–20 (1993); Hershey, J., *Ann. Rev. Biochem.*, 60:717–755 (1991)). The growth-inhibiting property of PKR can partly account for its apoptosis-inducing potential in some systems. An additional biological function for PKR is its putative role as a signal transducer. PKR plays a critical role in mediating the induction of IFN-α and IFN-β transcription by dsRNA or viruses (Der and Lau, *Proc Natl Acad Sci USA*, 92:8841–8845 (1995)). PKR has also been demonstrated to phosphorylate I-κBα leading to the release and activation of the transcription factor NF-κB (Kumar, A. et al., *Proc Natl Acad Sci USA*, 91(14):6288–92 (1994)).

According to one embodiment of the present invention, a method of treatment for tumors or cancer cells is disclosed. PKR gene and capable of expressing the PKR gene, and preferably administering TNF as a secondary agent to increase the level of TNF in the body of a cancer patient. Alternatively, poly I:C can be administered with or without TNF.

Administration of a PKR expression system to cancer cells increases the sensitivity of cells to chemotherapeutic agents, as well as TNF and poly I:C. It is commonly believed that by phosphorylating the eukaryotic translation initiation factor-2 (eIF-2), PKR inhibits further protein synthesis and thus contributes to the host viral defense. Consequently, high-expression (expression higher than endogenous expression in non-neoplastic cells) or over-expression (expression higher than endogenous expression in neoplastic cells) of PKR inhibits cancer cell growth or can induce apoptosis. The growth-inhibiting property of PKR accounts, in part, for its apoptosis-inducing potential and its ability to decrease cancer cell resistance to chemotherapeutics and to enhance sensitivity to of cancer cells to chemotherapeutics.

The PKR is preferably delivered to the cancer cells via an expression system designed to target a specific type of cancer. Expression system targeting can be accomplished by including a vector that encodes the PKR gene and is operatively linked and driven by a promoter that is associated or activated by the cancer cells to which the vector is delivered. Other methods of accomplishing tissue and tumor-specific expression are described herein.

A direct aim of gene therapy, generally, is targeting and transfer of the needed gene to the cells with a high degree of efficiency and specificity. The use of tissue-specific viral vectors for virus-related cancer cells is a useful means of targeting the therapy to the proper cells. Viral vectors, such as those associated with adenovirus, adeno-associated virus, papilloma virus, or hepatitis delta virus, are particularly useful in the method of the present invention, especially in connection with the treatment of virus-related cancer cells. Retroviral and adeno-associated vectors have been found to be particularly useful in some models for gene therapy. Examples of useful vectors, along with promoters, and suggested targeted cancer cells are presented below.

EXAMPLES OF VIRAL VECTORS WITH TISSUE-SPECIFIC PROMOTERS
USEFUL FOR TARGETING SPECIFIC CANCERS:

| Viral Vectors | Tissue-Specific Promoters | Corresponding Cancer |
| --- | --- | --- |
| A. General Vectors: Retrovirus, Adenovirus, Adeno-Associated Virus, and Vaccinia | CEA | CEA-expressing cells, e.g., G1 tumors, colorectal, lung *adenocarcinoma* |
| | HPV-E5, HPV-B7 | HPV-expressing cells, e.g., cervical *carcinoma* |
| | α-FP | α-FP expressing tumors, e.g., *hepatocarcinoma* |
| B. Tissue-specific Vectors (defective in replication) | | |
| Defective HDV | α-FP | α-FP expressing tumors, e.g., *hepatocarcinoma* |
| Defective HBV | α-FP | α-FP expressing tumors, e.g., *hepatocarcinoma* |
| Defective HPV | HPV E5 and HPV E7 | HPV-expressing cells, e.g., cervical *carcinoma* |

More specifically, practice of the method can induce cancer cells to undergo apoptosis. Tumor regression, cell death or apoptosis of cancer cells can be accomplished by administering to a patient in need thereof a nucleic acid encoding the The specificity of the viral vectors used can be determined by their biological properties, e.g. which tissues are infected, or by the tissue-specific nature of the promoter, which determines the expression of PKR or a combination of tissue-specific promoter and tissue-specific vector (viral or non-viral). There are many control measures which serve to maximize tumor specificity, such as (i) the tissue-specific nature of the vector, (ii) the specific functional promoters in the respective tumor cells, (iii) deployment of exogenous or endogenous TNF (including transfection of cancer cells with vectors expressing TNF and PKR in a tumor-specific fashion), and (iv) controlled activity of exogenous poly I:C for activating PKR or vector-encoded double stranded RNA.

Miyanohara, A. et al., *Gene Therapy*, 2:138–142 (1995), incorporated herein by reference, teaches gene therapy and in vivo transduction with retroviral vectors. Furthermore, Boviatsis, E. et al., *Human Gene Therapy*, 5:183–191 (1994), incorporated herein by reference, presents advantages and disadvantages of vectors derived from retrovirus, herpes simplex virus type 1, and adenovirus, for gene transfer in a brain tumor model and one skilled in the art may select such systems for use in the practice of the invention. Human papilloma virus is an effective tumor-specific vector associated with the development of cervical carcinoma, as shown by Cuthill, S. et al., in *Molecular Carcinogenosis*, 8:96–104 (1993) and can be used with the invention. The method and expression system of the present invention also include utilization of a plasmid as a vector to transport the PKR gene to the cancer site. For example, plasmid vectors that may be used for PKR insertions include pRC/CMV and pcDNA3 (In Vitrogen, San Diego, Calif.).

Important considerations in selecting a vector include site-specific and efficient gene transfer in light of the targeted cell and the treatment of a particular indication, the mode of delivery, and induction of apoptotic response.

Hepatitis delta virus (HDV) can be used as an example of a tissue-specific viral vector for the delivery or insertion of PKR into target cancer cells. The HDV genome is a small single-stranded RNA of about 1.7 kb in length. It has previously been demonstrated that exogenous gene sequences can be inserted into the HDV RNA genome without inhibiting HDV replication. (Hsieh, S. et al., *Innovations in Antiviral Development and Detection of Virus Infection*, pp. 125–128 (1992)). Thus, this vector can be used for the delivery of PKR specific for HBV infected cells, e.g., hepatitis B and hepatitis B-related hepatocarcinoma cells.

In some instances it will not be necessary to use a viral vector, non-viral vector or expression system that is tissue specific because the vector can be locally administered to the tumor. For example, vectors encoding PKR can be directly injected or topically applied to tumors, especially solid tumors.

The method of treating cancer cells and the expression system of the present invention provide a further advantage in that the specific activation of the expression of PKR can be controlled by a tumor-specific promoter. Thus, an activator known to be present in the cancer cell drives expression of the PKR from a vector when that vector has been introduced to the cell, as through transfection of the cell via a vector as described above. Usually expression will be enhanced due to modulation of a promoter region controlling expression of the PKR insert in the vector or a nucleic acid integrated into the DNA of the cancer cell. This tumor-specific gene expression is another means of ensuring that the proper cells receive the needed therapy and that administration or activation of PKR activity to normal cells or non-neoplastic cells is minimized. Promoters useful in the practice of the present invention include tissue specific promoters, such as CEA, α-FP, and E7.

The CEA promoter can be used to target PKR expression to cancer cells, as described herein. Carcinoembryonic antigen, or CEA, is a heavily glycosylated protein found at high levels in serum in association with certain cancers, especially those of the gastrointestinal tract, such as colon carcinomas. CEA has multiple transcription start sites and is a strong promoter Willcocks, T. C. et al., *Genomics*, 8:492–500 (1990); Schrewe, H. et al., *Mol. & Cell Bio.*, 10:2738–48 (1990)). As demonstrated by Osaki et al., *Cancer Research*, 54:5258–61 (1994), the use of the cell type-specific promoter of the CEA gene provides an effective gene therapy treatment of a CEA-producing adenocarcinoma of the lung. Further, DiMaio et al., *Surgery*, 116:205–13 (1994), teach directed gene therapy in vivo by coupling the CEA promoter to a herpes simplex virus thymidine kinase (HSV-tk) gene, which is specifically expressed in cancer cells, for treatment of cancer. CEA promoters are preferably used to direct the expression of PKR activity in specific cancer cells that express CEA proteins. This refers to any cancer cells that are active in the synthesis of the CEA proteins. Examples of target cancer cells include, but are not limited to, colorectal carcinoma (Gold, P. et al., *J. Exp. Med.*, 121:439–462 (1965)), lung adenocarcinoma (Osaki, T. et al., *Cancer Res.*, 54:5258–5261 (1994)), pancreatic carcinoma or other gastrointestinal tumors (Warshaw, A. et al., *N. Engl. J. Med.*, 326:455–465 (1992)), and ovarian tumors (Motoyama, T. et al., *Cancer*, 66:2628–35 (1990)).

In another embodiment, a PKR expression system can be constructed using a polynucleotide encoding PKR operably linked to a CEA promoter and a vector. The tissue specificity of these tumor-specific promoters has been illustrated by Osaki et al., *Cancer Res.* 54:5258–61 (1994), for instance. In this study, CEA-producing human lung cancer cells (A549), and non-CEA producing cells (lung cancer CADO-LC9 and HeLa) were transfected with a plasmid encoding the HSV-tk gene driven by a CEA promoter. Subsequent treatment of the HSV-tk transfectants with ganciclovir demonstrated that only CEA-expressing A549 cells were sensitive to the drug, with a thousand-fold increase in sensitivity. Consequently, the invention can be practiced with CEA promoters to achieve specific tumor targeting.

The alpha-fetoprotein, also known as α-FP or AFP, promoter provides a similar tumor-specific means of activating expression of PKR from a vector. Ido, A. et al., *Cancer Research*, 55:3105–09 (1995), have demonstrated the usefulness of the α-FP promoter in connection with the HSV-tk gene in a retroviral vector for treatment of hepatocarcinoma cells, wherein α-FP producing hepatoma cells which were infected with the gene exhibited an increased chemosensitivity as a result of expression of the HSV-tk gene. Such promoters are preferably used to treat tumors expressing α-FP. These tumors include hepatocarcinoma, hepatoma, and possibly α-FP expressing embryonal cancers.

For example, a PKR expression system can comprise a polynucleotide encoding PKR operably linked to a αFP promoter in a vector, e.g. a retrovirus. It is known in the art that a hybrid gene consisting of herpes simplex virus thymidine kinase (HSV-tk) gene under the control of human alpha-fetal protein (αFP) gene promoter can be inserted into gene-transfer viral vectors, including, e.g. retroviruses (Ido A. et al., *Cancer Res.* 55:3105–3109 (1995)). The specificity of the αFP promoter will cause the HSV-tk gene product or PKR protein to be expressed only in liver cancer cells. Similarly, other tissue-specific promoters can be used to specifically direct transcription of the encoded protein in gene transfer vectors, e.g., HPV-E5, HPV-E7, and CEA (Shillitoe, E. J. et al., *Cancer Gene Therapy* 1:193–204 (1994)). Such promoters or activating reagents can be discovered in the future by selecting and identifying regions of genes specifically expressed in a particular tumor type.

Other useful tumor-specific promoters for PKR expression are HPV promoters including, but not limited to, E5 and E7, which encode oncoproteins. The E6 and E7 promoters are especially useful in connection with HPV, or the human papilloma virus, for the treatment of human cervical carcinoma. Shillitoe, E. J. et al., *Cancer Gene Therapy*, 1:193–204 (1994) present gene therapy strategies for treatment of human cancers that contain HPV, such as cervical carcinoma, including the use of an E7 promoter. Such promoters are preferably used to treat HPV-related malignancies including oral, cervical anogenital, and cervical cancers as well as respiratory papillomatsis. Dysplastic lesions prior to neoplasia development may also be included. Additionally, skin cancers in immunosuppressed patients may be due to HPV infection and may, therefore, be suitable for treatment according to the present invention. Similarly, the promoter of herpes virus 8, which is the putative inducer of Kaposi's Sarcoma, can be linked to PKR for treatment of the tumor in AIDS patients. (Ganem et al., *Nature Medicine*, March 1996)

Thus, the above examples demonstrate the useful and practical nature of the use of tumor-specific promoters that can be utilized in combination with the PKR system described herein. The viral vector or plasmid used to deliver the PKR gene is preferably replication-defective and useful for the purpose of delivering a gene to a eukaryotic cell. Replication-conditional vectors, such as those which replicate only in rapidly-dividing tumor cells may also be used, as described in Boviatsis, E. et al., *Human Gene Therapy*, 5:183–191 (1994).

The method of treatment of the present invention is also directed to killing cancer cells or inhibiting tumor growth. Killing of cancer cells, as used here, can comprise induction of apoptosis, a mode of cell death that is more controlled than necrosis. Targeted elimination of the cells by apoptosis, according to the claimed method, minimizes the likelihood of sudden, massive tumor lysis and inflammatory response.

The treatment may be performed on many different types of cancers. For example, human colorectal cancer, human pancreatic cancer, human lung cancer, and human hepatocarcinoma may be treated in combination with the appropriate tumor-specific vectors and tumor-specific promoters, as discussed above.

Delivery of the expression system is generally by infection with the corresponding, specific viral vector for each tumor. For example, adeno-associated, retroviral, or HPV viral vectors encoding HPV-E7 promoter driving PKR may be used for HPV-infected cervical carcinoma. In another example, adeno-associated virus with CEA promoter may be used for treatment of CEA-expressing colonic carcinoma.

According to one embodiment of the present invention, after delivery and subsequent expression of the PKR gene, the targeted cancer cell is exposed to a secondary agent to further enhance apoptosis. The cancer cells expressing the PKR gene have an increased chemosensitivity to secondary agents such as TNF-α or poly I:C. Poly I:C is a synthetic double-stranded RNA, specifically polyriboinosinic acid reversibly bound to polyribocytodylic acid. It is representative of viral nucleic acid intermediates during virus replication and of secondary structures of some cellular RNAs. Either of these agents may be administered to the patient in a low dose to effect apoptosis. Alternatively, an RNA sequence capable of forming a dsRNA structure or its corresponding cDNA can be added to the vector together with the PKR gene. This will obviate the addition of exogenous poly I:C.

The ability of the invention to provide a low dosage is a particularly important advantage with respect to TNF administration. As discussed above, a high level of TNF is generally detrimental and causes undesirable side effects. With the method of the present invention, a relatively low dose of TNF may be administered. In Examples 1–4 and 7 (FIGS. 3–7 and 9) below, 0.5 ng/mL, or 10 units, of TNF was effective in inducing cell death in U937 cells and HeLa cells. One ng/ml of TNF-α equals 20 units of TNF-α/ml. One unit of TNF-α is defined as the concentration of TNF-α that can induce cytopathic effects (leading to death) in 50% of L929 cells (murine fibrosarcoma line) treated with the said concentration of TNF in the presence of 1 μg/ml actinomycin D for 24 hours at 37° C. (Matthews N. et al., *Lymphokines and Interferons: A Practical Approach*, IRL Press, 221 (1987)). Another advantage of the method is that the interstitial tissue TNF levels within the patient needing treatment can be sufficiently high, due to the patient's immune response to the cancer, so that exogenous TNF administration is unnecessary in patients with sufficient immune responses.

In previous clinical studies on the use of TNF-α in patients with cancer, the dose of TNF ranged between 50 $\mu g/m^2/d$ to 500 $\mu g/m^2/d$ (approximately 2 million units per day to 20 million units per day for adult patients), Brackowski, D. et al., *J Biological Regulators and Homeostatic Agents*, 8:77–80 (1994); Schiller, J. et al., *Amer J. Clin Oncology*, 18:47–51 (1995); Seibel, N. et al., *J Immunotherapy with Emphasis on Tumor Immunology*, 16:125–31 (1994). TNF, when administered to cancer cells expressing PKR via an expression system, can be dosed at a level two to three times lower, preferably five, 10 or 20 times lower and more preferably 100 times lower than the 50 $\mu g/m^2/d$ to 500 $\mu g/m^2/d$ range. TNF includes analogs of TNF, such as truncated forms or isoforms of TNF that mimic the activity of TNF in cells, especially cancer cells.

The immunomodulator can be administered by intravenous, intramuscular administration or by local perfusion of the limb where the solid tumors are located. The duration of therapy ranged from a few days to a longer period of time.

In studies with very high TNF doses up to 500 $mg/m^2$ of total dose, there were significant toxicities (Vaglini, M. et al., *Cancer*, 73:483–92 (1994); Lejeune, F. et al., *J. Cellular Biochem*, 56:52–61 (1994)). In these studies, patients developed a septic-like shock syndrome with some of them progressed to multi-organ-failure syndrome (Vaglini M. et al., *Cancer*, 73:483–92 (1994); Seibel, N. L. et al., *J. Immunotherapy*, 16:125–31 (1994)).

Thus, it has been concluded that while TNF-α is effective as a tumoricidal agent at high doses, it is too toxic for general use in cancer patients and undesirable for therapeutic uses. Generally, TNF doses practiced with the invention will be less than 100 $mg/m^2$ total dose, preferably less than 20 $mg/m^2$ and more preferably less than 5 $mg/m^2$ in total dose.

The method described here would allow for the use of TNF-α or similar cytotoxic agents in cancer therapy. With the over-expression of PKR activity in target tissue-specific tumor cells, TNF can be used at lower concentrations. Alternatively, TNF can be used in combination with other chemotherapeutic agents, e.g. taxol in human ovarian cancer (Berkova, N. et al., *Anticancer Research*, 15:863–66 (1995).

In another embodiment, the invention can be practiced with poly I:C. Poly I:C includes analogs of polyinosinic acid and polycytidylic acid and any other double-stranded nucleic acid currently available or developed in the future that can stimulate double-stranded RNA kinases. Such analogs can have different bases or modified I's or C's and/or modified linkages between the nucleotides. The dosage for poly I:C or its analog Ampligen is measured in vivo by methods established for the use of commercially available poly I:C. Usually, poly I:C is a double-stranded RNA composed of polyinosinic acid binding in a complementary manner to polycytidylic acid. Double-stranded RNA intermediates are required as a co-factor for the activation of PKR enzyme activities. To minimize toxicity from poly I:C, a commercially available poly I:C such as Ampligen [poly $(I)_n$:poly$(C_{12}U)_n$] can be used. The dosage of Ampligen used clinically ranges from 10 to 570 mg/m²/dose, twice weekly for 9 to 25 weeks (Reference: Armstrong J. A., *J Infect. Dis.*, 166:717–722 (1992)). Poly I:C, when administered to cancer cells expressing PKR via an expression system, can be dosed at a level 2 to 3 times lower, preferably 5, 10 or 20 times lower and more preferably 100 times lower than the 10 µg/m²/d to 570 µg/m²/d. In vitro, the effective concentration of Ampligen or poly I:C for biological activation of PKR is in the range of µg/ml. (Ushijima H. et al., *J Inteferon Res*, 13:161–171 (1993)).

With respect to in vitro drug screening applications, since PKR-overexpressing cells (e.g. U9K-S, -HeK-S) are particularly sensitive to TNF effects, these cells can be used as indicator cell lines to evaluate the efficacy of apoptosis-inhibitors in mitigating or suppressing the effects of TNF. In this embodiment, TNF or TNF-inducing agents are used in conjunction with an apoptosis-inhibitor to treat selected cell types to be examined. The supernatants and the cells are examined for the presence of TNF (by ELISA) by conventional methods as well as by PKR-over expressing cells. This cell line system then provides a sensitive and efficient functional assay to screen the efficacy of a variety of apoptosis-inhibitors. Thus, the PKR(+) cells can be used to examine the relative potency of agents that are capable of inducing apoptosis.

While the method described specifically uses TNF-α as an inducer for PKR activity leading to apoptosis of target cells, the same principle applies to the use of other cytokines that can activate PKR activity, e.g. IFNs, PDGF, TGF, and EGF. The present invention can be also applied to the interferons (IFNs), which are naturally-occurring proteins that are produced by immune cells in response to viral infections or tumor cells. IFNs mediate diverse biological processes including induction of antiviral activities, regulation of cellular growth and differentiation, and modulation of immune functions (Sen, G. et al. *J. Biol. Chem.*, 267:5017–5020 (1992); Pestka, S. et al.,*Ann. Rev. Biochem.*, 56:727–777 (1987); Lau, A., *Adv. Ped. Infect. Dis.*, 9:211–236 ((1994)). IFNs elicit their biological activities by inducing the expression of IFN-stimulated genes, or ISG. The best studied examples of ISGs include PKR or p68 kinase, 2'-5'-linked oligoadenylate (2-5A) synthetase, and ribonuclease L (Taylor, J. et al., *Virus Research*, 15:1–26 (1990); Williams, B. et al., *Biochem*, 200:1–11 (1991)).

IFNs belong to a class of negative growth factors having the ability to inhibit growth of a wide variety of cells with both normal and transformed phenotypes. IFN therapy has been shown to be beneficial in the treatment of human malignancies such as Kaposi's sarcoma, chronic myelogenous leukemia, non-Hodgkin's lymphoma, and hairy cell leukemia, as well as in the treatment of infectious diseases such as papilloma virus (genital warts) and hepatitis B and C (reviewed by Gutterman, *Proc. Natl Acad Sci.*, 91:1198–1205 (1994)). Methods of the invention can increase the effects IFNs in these cancers as well as others, allowing lower doses of IFN to be administered.

METHOD OF SCRENING AND ASSAY SYSTEM

The present invention also includes an assay system useful for identifying chemotherapeutic and immunomodulator compounds. According to this embodiment, a PKR tumor-specific expression system, as described above, is transfected into a cancer cell or series of cancer and non-neoplastic cells. The assay system thus comprises a cancer cell incorporating the expression system, which includes a plasmid or viral vector, and optionally a tumor-specific promoter, and a PKR gene operatively linked to a promoter and either the plasmid or the genome (or partial genome) of the viral vector. Expression of the PKR gene results because the expression system is driven by a promoter that is usually specific to the cancer cell utilized for the assay system. The cells expressing PKR can be used, in small portions, to test numerous possible chemotherapeutic compounds.

More particularly, the method of screening includes the step of observing the transformed cancer cells before and after the addition of each candidate compound cancer cells showing indications of apoptoses enables the identification of new compounds useful for chemotherapy. Observations may be by light or electron microscopy, or by analysis of DNA fragments, or RNA levels, for example, as discussed in the examples below. Other assays of cell metabolism, as described herein or known in the art can be used to detect changes in cellular processes caused by the compound added to the PKR expressing cancer cells.

Although expression of PKR in the cancer cells results in a certain level of apoptosis, the primary result is an increase in chemosensitivity of the cancer cells so that contact with an appropriate chemotherapeutic agent causes increased apoptosis and, consequently, easily observable results.

COMPOSITIONS

According to one embodiment, the method of the present invention produces PKR expression plasmids or viral vectors that are active predominantly in the cancer cells compared to normal cells. For example, HBV and HPV would be useful for HBV-related hepatocarcinoma and HPV-related cervical carcinoma, respectively. This embodiment relies upon the use of PKR-expression plasmids or specific viral vectors as the source of the PKR gene for transfection or infection of the cancer cells. For example, an HBV which is defective for replication itself can encode PKR that is, in turn, driven by an HBV-specific promoter. This construct is then used to infect HBV-related hepatocarcinoma cells. This results in specific activation of PKR expression only in HBV-infected cells, leading to the onset of apoptosis. Further enhancement of apoptosis can be achieved by treating the PKR-over-expressing cells with TNF or poly I:C, as discussed above. In summary, one aspect of this embodiment includes designing a PKR expression plasmid by (a) constructing a replication-defective viral vector specific for the respective virus-related cancer, (b) constructing an expression plasmid encoding PKR driven by the respective virus-specific promoter, (c) inserting the plasmid encoding PKR driven by the virus-specific promoter into the viral vector, and (d) purifying the viral vector for in vitro or therapeutic uses. The method of using this expression system comprises introducing the plasmid to the targeted cancer cells, optionally followed by contacting the cancer cells with a secondary agent such as TNF-α, poly I:C, or other chemotherapeutic agents.

Cells can be induced to undergo apoptosis by manipulating the expression or activity of PKR that normally regulates expression in vivo. Suppression or elimination of the expression or activity of PKR will result in less cell death upon treatment with apoptosis-inducing agents. On the other hand, enhancing the expression or activity of PKR will result in a higher than normal level of apoptosis of the cells. One result of this higher than normal expression of PKR is that viral vectors encoded with PKR driven by virus- or cancer-specific promoters can be used as gene therapy agents to target select cancer or virus-infected cells to induce death of the respective cells.

The examples below demonstrate that for cancer cells, such as the promonocytic tumor cell line U937, (i) overexpression of PKR alone was enough to induce apoptosis, (ii) TNF-α induced cytotoxicity can enhance apoptosis, (iii) TNF-α induced PKR, and (iv) PKR was pivotal in the TNF-α-induced apoptotic pathway.

The demonstration of chromatin condensation and oligonucleosomal DNA ladder in the TNF-α-treated U9K-C cells are indicative of apoptosis (Wyllie, A. et al., Histochem J, 13:681–92 (1981) and Earnshaw, W., Curr Opin Cell Biol, 7:337–43 (1995) brought on by the TNF-α treatment. That TNF-α exerted its cytotoxicity on U937 cells primarily through apoptosis rather than necrosis is consistent with recently published data on the ability of TNF-α to induce either necrosis or apoptosis in tumor cells Laster, S. et al., J Immunol, 141:2629–34 (1988)). The finding that TNF-α can induce apoptosis depending on the cell type and the presence of metabolic inhibitors (Laster, S. et al., J Immunol, 141:2629–34 (1988) and Grooten, J. et al., Cytokine, 5:546–55 (1993)) suggests that some cell types may be susceptible to one but not the other cytotoxic action of TNF-α. Conceivably, this may be partly due to (i) the inherent cellular properties and the physiological state of the target cells when TNF-α is applied, and (ii) the presence or absence of functional TNF-α receptor subunits associated with TNF-α-induced cytotoxicity.

No overt cell death in U9K-C cells was evident by either light microscopy or trypan blue exclusion staining (FIGS. 3 and 5, respectively) after an 18 hour TNF-α treatment. Yet data from electron microscopy studies (FIG. 4) and oligonucleosomal DNA ladder analysis (FIG. 6) unequivocally showed the commitment of TNF-α-treated U9K-C cells to apoptosis, a process that invariably leads to eventual cell death. This apparent inconsistency was probably due to the relatively low concentration of TNF-α used (0.5 ng/mL), the short incubation period with TNF-α (18 hours), or some undefined intrinsic anti-apoptosis mechanisms delaying the onset of apoptosis. Consequently, the TNF-α-treated cells were either at too early an apoptotic stage, or, the proportion of apoptosing cells was at too low a level to be significantly detected by both light microscopy and viable cell counts. These arguments are further supported by the observations that (i) DNA fragmentation occurs before actual cell death (Wright, S. et al., J Cell Biochem, 48:344–55 (1992)), (ii) trypan blue stains only dead cells, and (iii) prolonged TNF-α treatment (48 hours) did render overt cell death in U9K-C cells demonstrable by light microscopy and trypan blue exclusion staining.

An over-expression of PKR was enough to induce apoptosis in U937. Although it was a slow process, this PKR-induced apoptotic pathway could be hastened by poly I:C, an activator of PKR. This result is a direct proof of the apoptosis-inducing potential of PKR in U937 cells. Additionally, PKR overexpression induces cell death in HeLa cells (FIG. 9)

Figure 9A:
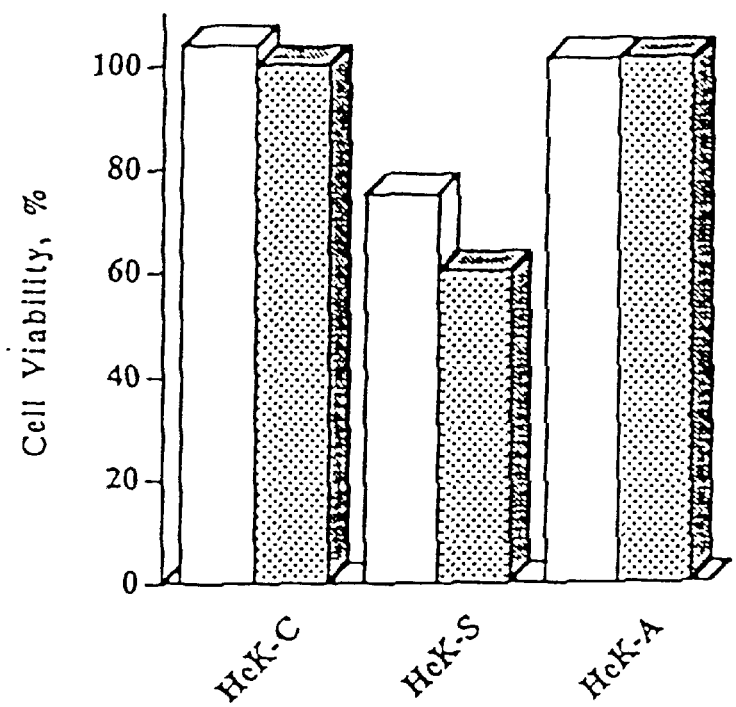
FIGS. 9A–9C illustrate the viability of HeLa cells after TNF-α treatments. HeLa (human cervical carcinoma) cells were treated with TNF-α for the times indicated and were diluted five-fold with 0.4% trypan blue in PBS for viable cell counts, as in FIGS. 5A1–5D. The results are expressed as percentages of viable cell counts of untreated cells, and are representative of experiments performed at least three times.
Figure 9B:
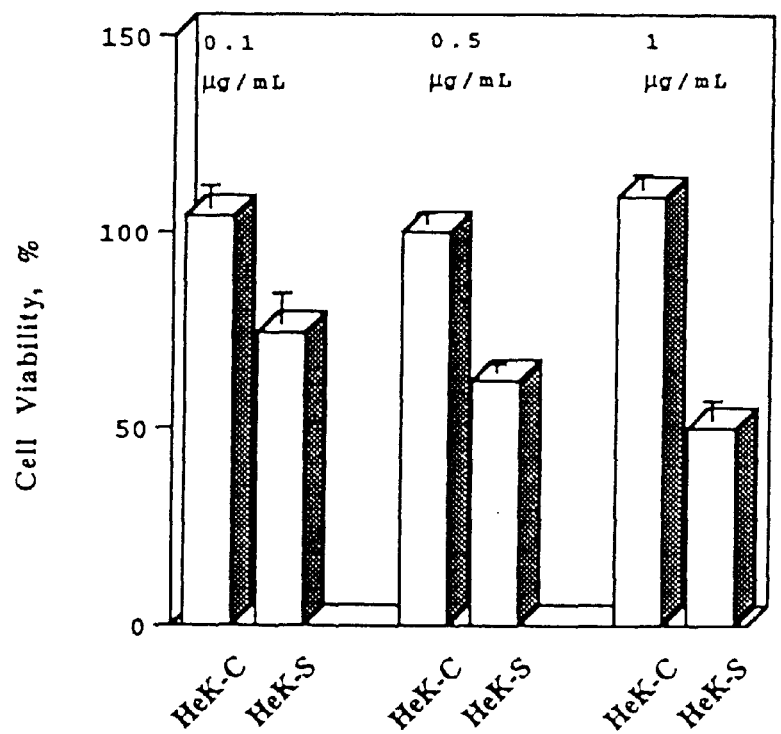
Figure 9C:
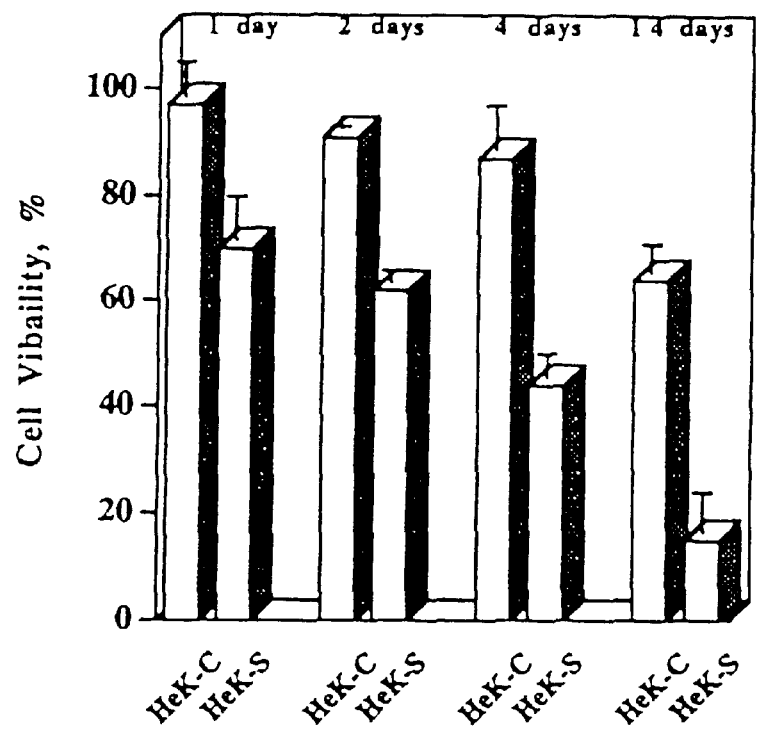

Similar to results on U937 cells, the apoptosis-inducing effects of TNF-α in HeLa cells occurred in a dose-dependent manner. Even employing very low doses of TNF in addition to poly I:C, at least 80% of the PKR-overexpressing HeLa cells died spontaneously (FIG. 9C).

TNF-α is known to activate (i) phospholipases A2, C and D (Suffys, P., Beyaert, R., De Valck, D., Vanhaesebroeck, B., VanRoy, F. & Fiers, W., Eur J Biochem, 195:465–75 (1991); Schutze, S., Berkovic, D., Tomsing, O., Unger, C. & Kronke, M., J Exp Med, 174:975–88 (1991); De Valck, D., Beyaert, R., VanRoy, F. & Fiers, W., Eur J Biochem, 212:491–7 (1993)), (ii) serine/threonine phosphatases (44), (iii) the 2'-5'-oligoadenylate (2-5A) synthetase to synthesize 2-5A, which in turn activates the RNase L that degrades viral mRNA (45, 46), (iv) the PKC pathway which leads to phosphorylation of serine/threonine kinases (Van Lint, J., Agostinis, P., Vandervoorde, V., Haegeman, G., Fiers, W., Merlevede, W. & Vandenheede, J. R., J Biol Chem, 267:25916–21 (1992); Schutze, S., Berkovic, D., Tomsing, O., Unger, C. & Kronke, M., J Exp Med, 174:975–88 (1991); Vietor, I., Schwenger, P., Li, W., Schlessinger, J. & Vilcek, J., J Biol Chem, 268:18994–9 (1993)), and (v) the sphingomyelin pathway generating the second messenger ceramide, which in turn leads to activation of NF-κB (48–50). TNF-α has also been shown to upregulate IRF-1 (Fujita, T., Reis, L. F., Watanabe, N., Kimura, Y., Taniguchi, T. & Vilcek, J., Proc Natl Acad Sci USA , 86:9936–40 (1989)), a transactivator of many genes involved in the IFN signaling pathway and a direct upregulator of the PKR gene itself (Kirchhoff, S., Koromilas, A. E., Schaper, F., Grashoff, M., Sonenberg, N. & Hauser, H., Oncogene, 11:439–45 (1995)). Thus, the apoptosis induction potential of IRF-1 as reported recently (Tamura, T., Ishihara, M., Lamphier, M. S., Tanaka, N., Oishi, I., Aizawa, S., Matsuyama, T., Mak, T. W., Taki, S. & Taniguchi, T., Nature, 376:596–9 (1995)) may actually turn out to be a consequence of induction of PKR and its pathway of death by IRF-1. Taken together, manipulation of IRF-1 by TNF-α to induce apoptosis is also within the scope of the present invention, since TNF induces both PKR and IRF-1. One potential mechanism is the inhibition of protein synthesis through the phosphorylation of eIF2 by PKR, so that a prolonged and uncontrolled activation of PKR will adversely affect normal cell functions leading eventually to cell death. An activating agent such as dsRNA hastens the cell death process.

EXAMPLES

The following examples of the present invention are provided to illustrate the invention in more detail. The examples are to be taken as illustrative only, without limiting the scope of the invention.

METHODS

WESTERN BLOT ANALYSIS

Total protein extracts (20–30) μg per sample in PBS containing 1% NP-40, 0.5% sodium deoxycholate, 0.1% SDS, 0.1 mg/mL phenylmethylsulfonyl fluoride, 1 mM sodium orthovanadate and 45 μg/mL aprotinin, all Sigma chemicals) were separated by SDS/10% PAGE, electroblotted onto nitrocellulose membranes, and were probed with anti-PKR (Der and Lau, Proc. Nat. Acad. Sci., 92:8841–45 (1995)), or anti-actin antibodies (Sigma) using the ECL (Amersham) chemiluminescence system and following the manufacturer's protocol.

PREPARATION OF PLASMIDS

Sense and antisense PKR expression vectors derived from the parental control expression vector pRC-CMV (Invitrogen) have been described, as well as methods to isolate and characterize clonal cell lines derived from ATCC U937 cells and containing the three PKR vectors (Der and Lau, *Proc. Nat. Acad. Sci.*, 92:8841–45 (1995)). Briefly, cDNA inserts corresponding to the wild type human PKR gene from the plasmids pBS-8.6R (Meurs E. et al., *Cell*, 62:379–90 (1990)) was released by HindIII digestion and subcloned into pRC-CMV (Invitrogen), a constitutive eukaryotic expression plasmid containing a G418-resistance marker. The orientation of the inserts in selected clones was determined by restriction digest analysis and confirmed by sequencing (Sequenase 2.0, USB). This procedure resulted in the isolation of the expression plasmids used, pCMV-PKR (containing PKR cDNA in the sense orientation), pPKR-AS (containing the PKR cDNA in an antisense orientation). Expression of the respective PKR coding sequence is under control of the CMV promoter in the respective vector. Both old and new U937 derivatives were isolated for this work.

The pRC/CMV plasmid (Invitrogen) is commonly used for eukaryotic expression. The vector offers the following features suitable for PKR transcription: (i) promoter sequences from the immediate early gene of the human CMV (cytomegalovirus) for high level transcription, (ii) polyadenylation signal and transcription termination sequences from bovine growth hormone (BGH) gene to enhance RNA stability, (iii) SV40 origin for episomal replication and simple vector rescue, (iv) T7 and Sp6 RNA promoters flanking the multiple cloning site for in vitro transcription of sense and antisense RNA, and (v) the ampicillin resistance gene (AMP) and ColE1 origin for selection and maintenance in *E. coli*. The vector also contains a G418 resistance marker (NEO) to allow for selection and identification of the plasmids after transfer to eukaryotic cells. The structure of pCMV-PKR is shown in FIG. 1.

Similarly, pHBC-PKR, pHBS-PKR pHPE5-PKR and pHPE7-PKR were prepared by replacing the CMV promoter from pCMV-PKR with the respective promoters from genes encoding HBV core antigen, HBV surface antigen (Zhou DX, Yen TSB, *J Biol Chem*, 265(34):20731–20734 (1990); Guo W. et al., *J Virol*, 65:6686–6692 (1991)), HPV E5 and HPV E7 genes (Hu G. et al., *Cancer Gene Ther*, 2:19–32 (1995)) respectively. The HPV strains used include, but are not limited to, serotype 16 and 18, which are believed to be common causative agents of cervical carcinoma and condyloma acuminata.

CULTIVATION AND ISOLATION OF PKR-EXPRESSING STABLE TRANSFECTANTS

Methods to isolate clonal cell lines derived from transfected cells containing the two PKR vectors have been described (Der and Lau, *Proc. Nat. Acad. Sci.*, 92:8841–45 1995). Stable transfectants were obtained by electroporation of $5 \times 10^6$ exponentially growing U937 (promonocytic), HeLa (cervical carcinoma), Hep3B (hepatocarcinoma), or Chang liver (non-malignant) cells with 10 µg of each plasmid, in serum-free RPMI-1640, with a Gene Pulser apparatus (BioRad). Bulk populations of stable transfectants were obtained by selection with 400 µg/mL geneticin (GIBCO-BRL) for 3 weeks. Clonal lines were subsequently obtained by limiting dilution cloning. Cell lines were cultured in RPMI-1640 ( for U937) or DMEM (for HeLa and Hep3B) media containing 5–10% fetal bovine serum (complete media) and 400µg/mL geneticin (Gibco/BRL). In the case of U937 clonal cells containing pRC-CMV, pCMV-PKR or pPKR-AS, expression vectors were designated U9K-C, U9K-S, and U9K-A, respectively.

INDUCTION OF APOPTOSIS AND CELL VIABILITY

To induce apoptosis, recombinant human TNF-α (R&D Systems, Minneapolis, Minn.) was added to the medium to a final concentration of 0.5–5 ng/mL. Alternatively, poly I:C, in an approximately 100-unit polymer size,(Pharmacia-LKB, Piscataway, N.J.) was used at a concentration of 0.1 µg/mL. To determine cell viability, cells were mixed with 0.4% trypan blue in a ratio of four volumes of cells in culture medium to one volume of the trypan blue and were counted with a hemocytometer.

MICROSCOPY STUDIES

For light microscopy, cells were diluted ten-fold with 0.5% neutral red. In addition, samples were prepared by standard procedure, as per Lau, A.S. et al. *AIDS*, 9:137–143 (1995), incorporated herein by reference, for ultrastructural examination. The cells were post-fixed in 1% osmium tetroxide, dehydrated for staining with uranyl acetate and lead citrate. Thin sections were examined in a JEOL 100 SX electron microscope (JEOL, Tokyo, Japan).

SMALL MOLECULAR WEIGHT DNA ISOLATION

Following treatment of cells with TNF-α or poly I:C, apoptotic DNA fragments were isolated according to Herrman et al., *Nucleic Acids Res*, 22(24):5506–07 (1994)). Briefly, cells were extracted twice with lysis buffer (1% NP-40, which is a mild detergent causing cell lysis, in 20 mM EDTA, 50 mM Tris-HCl, pH 7.5). After centrifugation at 1600×g, the combined supernatants were brought to 1% SDS, treated with a final concentration of 5 µg/µL of RNase A (Pharmacia-LKB) at 56° C. for 2 hr, and followed by digestion with a final concentration of 2.5 µg/µL proteinase K at 37° C. for 2 hr. Apoptotic DNA fragments were precipitated and analyzed in 1% agarose gels. More specifically, the cells were phenol-chloroform extracted for nucleic acids, which were further treated with Ribonuclease A (100 µg/mL; Sigma, St Louis, Mo.). The DNA samples were then phenol-extracted again and analyzed by electrophoresis on a 1% agarose gel containing ethidium bromide. The fractionated DNA samples were examined and photographed under UV light. A preparation of HaeIII-digested fX 174 DNA (Bethesda Research Lab, Gaithersburg, Md.) was used as a size marker.

REVERSE TRANSCRIPTION-POLYMERASE CHAIN REACTION (RT-PCR)

Total RNA extraction and RT-PCR for steady-state RNA levels was performed as described in Yeung, M. C. et al., *AIDS*, 9:137–143. Briefly, total RNA was obtained from frozen cells by the acid-guanidinium thiocyanate-phenol-chloroform method described in Chomczynski, P. et al.,*Anal Biochem*, 162:156–9 (1995). To perform reverse transcription-polymerase chain reaction (RT-PCR) analysis, first-strand cDNA was reverse-transcribed from total RNA. More particularly, in a 20 µl reaction, 1 µg of total, undegraded RNA and 100 ng of Random Primers (Promega, Madison, Wis.) were heated at 95° C. for 1 minute and cooled briefly on ice before adding 5× reverse-transcription buffer (250 mM Tris-HCl, pH 8.3, 375 mM KCl, 15 mM $MgCl_2$, 50 mM DTT), dNTP to a final concentration of 1.5 mM, 8 units of RNAguard (Pharmacia-LKB, Piscataway, N.J.) and 200 units of Moloney murine leukemia virus reverse transcriptase (Promega, Madison, Wis.). After 1 hour at 37° C., the reaction was terminated by heating at 95° C. for 5 minutes before cooling on ice. Amplification of the reverse-transcribed cDNA was accomplished by subjecting up to 5 µl of the cDNA to a 100 µl PCR reaction containing 50 mM KCl, 10 mM Tris-HCl, pH 9.0 at 25° C., 0.1% Triton X-100, 2 mM $MgCl_2$, 0.2 mM of each of the deoxyribonucleoside triphosphates (dNTP), 50 pmol of each primer, 2.5 units DNA Taq polymerase (Gibco/BRL, Grand Island, N.Y.) and 100 μl light mineral oil in a thermal cycler (Coy Corporation, Grass Lake, Mich.). The PCR reaction was allowed to proceed for 30 cycles (95° C. for 1 minute, 55° C. for 2 minutes, and 72° C. for 3 minutes) before the reaction was arrested in its logarithmic phase by rapidly cooling to 4° C. The PCR products were resolved on 0.7% agarose gel, followed by Southern blotting analysis (Southern EM., *J Mol Biol* 98:503–517 (1995)) with gene-specific probes. PCR primer sets used were: (i) Glyceraldehyde-3-phosphate dehydrogenase (GAPDH): upper, (SEQ ID NO:1) 5' CAAAAGGGTCATCATCTCTG 3'; lower, (SEQ ID NO:2) 5' CCTGCTTCACCACCT-TCTTG 3', (ii) PKR: upper, (SEQ ID NO:3) 5' GGCAC-CCAGATTTGACCTTC; lower, (SEQ ID NO:4) 5' TCCT-TGTTCGCTTTCCATCA 3', (iii) interleukin-1β converting enzyme (ICE): upper, (SEQ ID NO:5) 5' AATGCTGCTA-CAAAATCTGG 3'; lower, (SEQ ID NO:6) ATCATCCT-CAAACTCTTCTG 3', and (iv) 18S ribosomal RNA: upstream, (SEQ ID NO:7) 5' CGCAGCTAGGAATAATG-GAA 3'; downstream, (SEQ ID NO:8) 5' TTATGACCCG-CACTTACTGG 3'.

Example 1

PKR Expression Vectors and TNF-α Treatment in Neoplastic Cells Induces Formation of Apoptotic Bodies.

Figure 3:
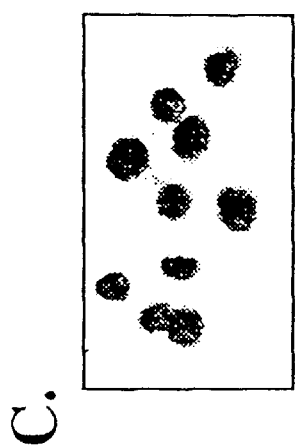
FIG. 3 shows light microscopy studies of U937 subclones treated with recombinant TNF-α. U937 subclones grown in 5% fetal bovine serum were treated with 0.5 ng/ml TNF-α for 18 hours, and then diluted ten-fold with 0.5% neutral red before examination by light microscopy. Panels A–C, are control subclones without TNF, U9K-C (parental vector only), U9K-S (vector with sense PKR insert), and U9K-A (vector with antisense PKR insert) cells, respectively. Panels D–F, TNF-α-treated (0.5 ng/ml; 18 hour) U9K-C, U9K-S and U9K-A cells, respectively. Magnification: ×100. Note the spontaneous cell death in untreated U9K-S cells (panel B) and the enhanced cell death and extensive cell debris in TNF-α-treated U9K-S cells (panel E). All cells were cultured in 5% fetal bovine serum. There were no significant differences in growth or killings when the concentration of serum was raised from 5% to 10%. Experiments were also performed in the absence of serum for 18 hours, showing an additional enhanced killing with TNF-α.
Figure 3:
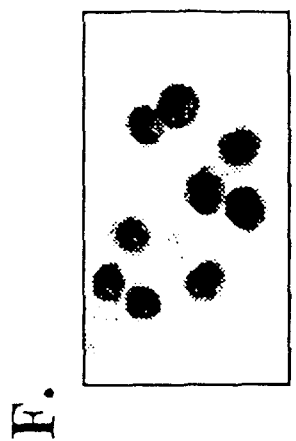
Figure 3:
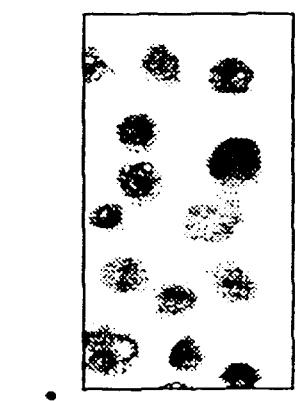
Figure 3:
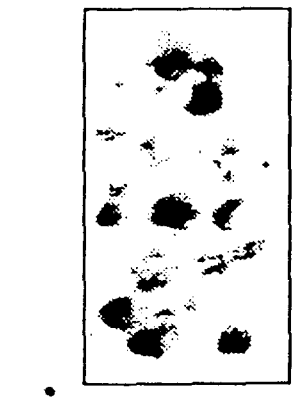
Figure 3:
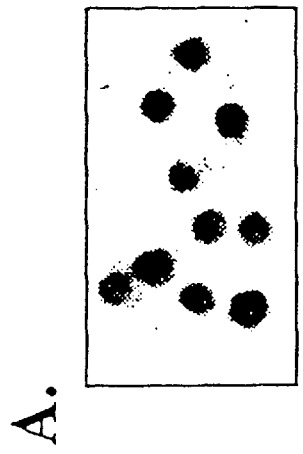
Figure 3:
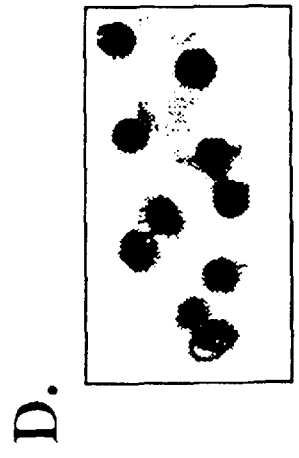

Three U937 subclones, i.e. a control (U9K-C), a subclone having a PKR-sense insert (U9K-S), and a subclone having a PKR-antisense insert (U9K-A), were first treated with 0.5 ng/mL TNF-α for 18 hours for possible cytopathic effects. FIG. 3 revealed that by light microscopy, both TNF-α-treated U9K-C and U9K-A cells did not exhibit any observable sensitivity to TNF-α, as seen in FIG. 3, panels D and F. However, with a 48-hour extended TNF-α treatment, U9K-C cells showed signs of cell injury including cell shrinkage, increased cellular granularity and cell debris (results not shown). U9K-A cells were relatively unaffected by even prolonged TNF-α treatment. In sharp contrast to U9K-C and U9K-A cells, the constitutively PKR-expressing U9K-S cells displayed a heightened susceptibility to TNF-α, as seen in FIG. 3, panels B and E. After only an 18 hour incubation with TNF-α, as shown in FIG. 3, these cells sustained considerable cell injury and changes in cell morphology similar to, but with a higher degree of severity, than exhibited by the U9K-C cells which were treated with TNF-α for 48 hours (results not shown for 48 hour treatment).

Figure 4:
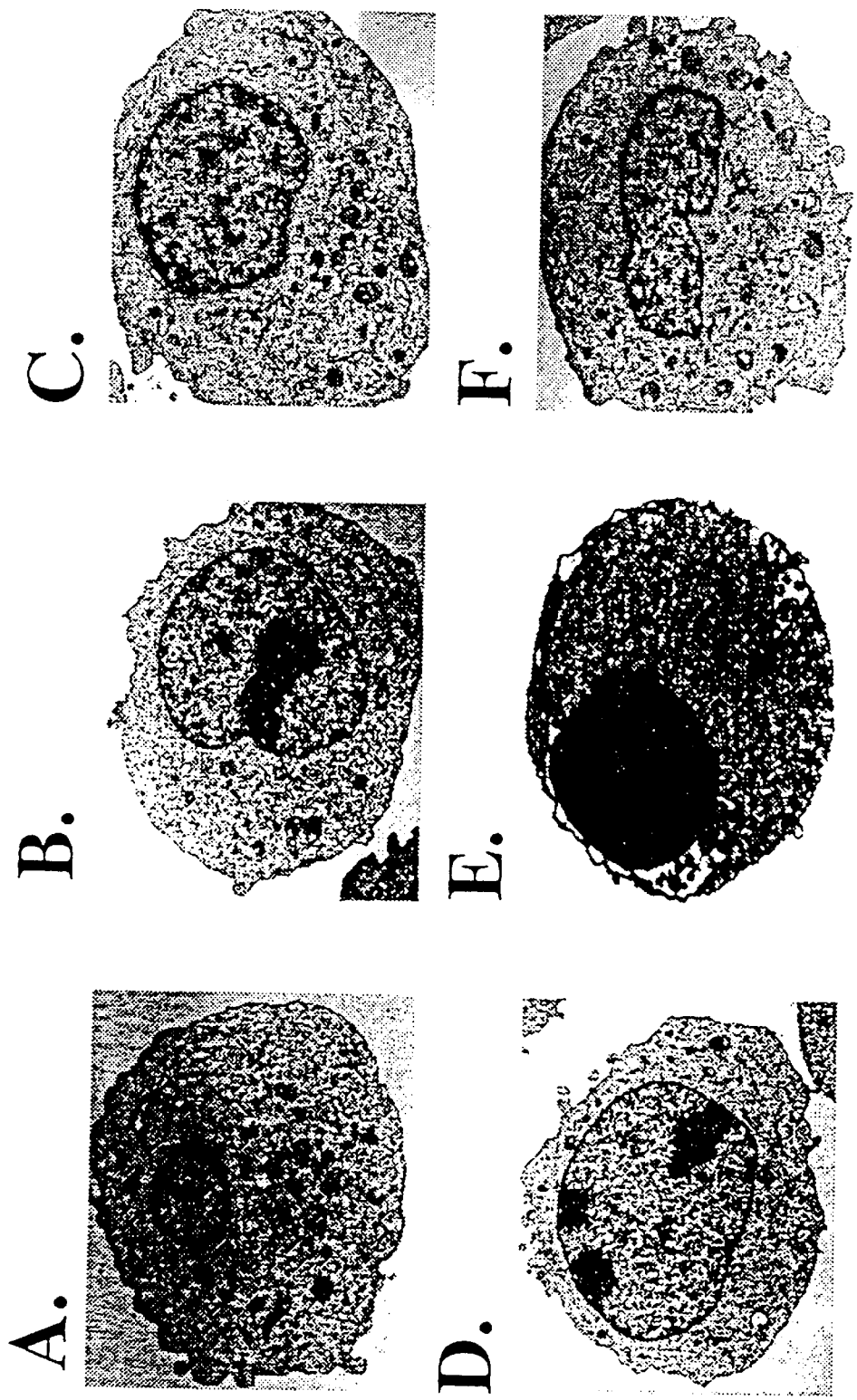
FIG. 4 shows electron microscopy of U937 subclones treated with TNF-α. U937 subclones were treated with 0.5 ng/ml TNF-α for 18 hour and processed for electron microscopy. Panels A–C show control subclones without TNF, U9K-C, U9K-S and U9K-A cells, respectively. Panels D–F show TNF-α-treated (0.5 ng/ml for 18 hours) U9K-C, U9K-S and U9K-A cells, respectively. Magnification: Panel E, ×82,000; other panels, ×41,000. Note the slight condensation of chromatin at the inner margin of the nuclear membrane of TNF-α-treated U9K-C in panel D. Panel E shows an apoptotic body of a TNF-α-treated U9K-S cells. U9K-A cells appear, in Panel F, to be resistant to TNF-α treatment.

By transmission electron microscopy, morphological changes were evident in the nuclei of both U9K-C and U9K-S cells after an 18-hour treatment with TNF-α, as seen in FIG. 4. These cytopathic effects were particularly pronounced for U9K-S cells. The condensation of chromatin into crescents juxtaposing the inner nuclear membrane was clearly seen in these cells, which is suggestive of apoptosis. While these chromatin crescents were induced in U9K-C cells only after TNF-α treatment, they were formed spontaneously at a low level in U9K-S cells. Consistent with the light microscopy results described above, this chromatin condensation was dramatically enhanced by TNF-α treatment in U9K-S cells. Significantly, no appreciable nuclear condensation was apparent in the U9K-A cells in the presence of TNF-α, as seen in FIG. 4, thus establishing a crucial role of PKR in TNF-α-induced cytotoxicity in U937 cells. Interestingly, with continuous routine subculturing and even in the absence of TNF-α, U9K-S cells replicated at a slower rate than the other two U937 subclones and tended to undergo spontaneous cell lysis. Thus, a given culture of U9K-S cells would eventually die out after about 4 to 5 months of continuous sub-culturing. The cytopathic effects exhibited by the U937 cells was TNF-α specific, since anti-TNF-α antibodies abrogated the TNF-α-induced morphological changes.

Example 2

TNF-α and Poly rI:rC, in Combination with PKR, Have a Negative effect on U937 Cell Viability.

Figure 2A:
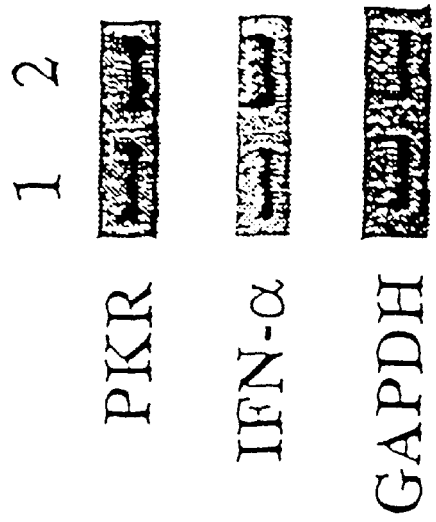
FIG. 2A shows steady-state mRNA levels of PKR and IFN-α in U937 subclones. Total RNA was extracted from U9K-C and U9K-S cells harboring control and constitutive PKR expression vectors, respectively, and was subjected to RT-PCR analysis for steady-state PKR and IFN-α messages. The vector used was pCMV-PKR. Lanes 1 and 2, U9K-C and U9K-S cells, respectively. Lane 2 shows at least an estimated 10% increase of mRNA over Lane 1. GAPDH messages served as PCR internal controls.
Figure 2B:
FIG. 2B shows a western blot analysis of PKR in U937 subclones. Total cytoplasmic proteins were extracted from U9K-C and U9K-S cells harboring control and constitutive PKR expression vectors, respectively, and subjected to western blot analysis using the luminol chemiluminescence method and done according to the manufacturer's (Amersham's) protocol. Lane 1 shows U9K-C cells and lane 2 shows U9K-S cells. GAPDH proteins in each sample served as internal controls for even protein loading.
Figure 2B:
Figure 5A:
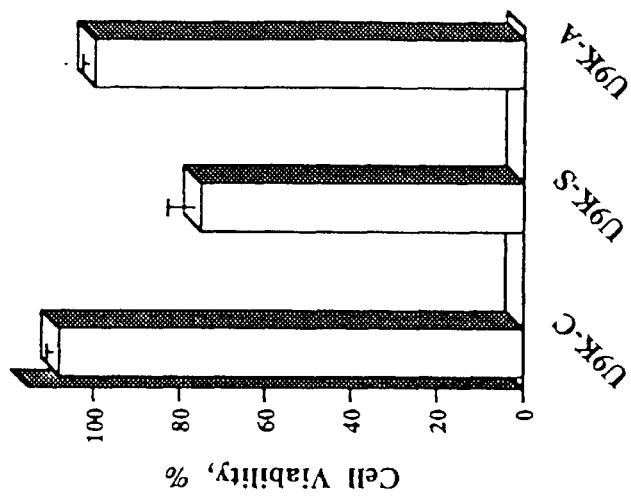
Figure 5A:
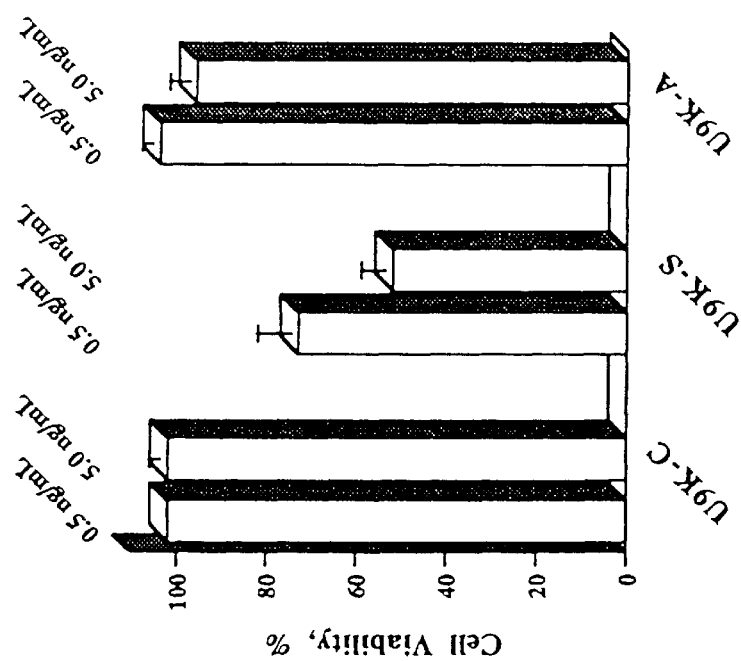
Figure 5B:
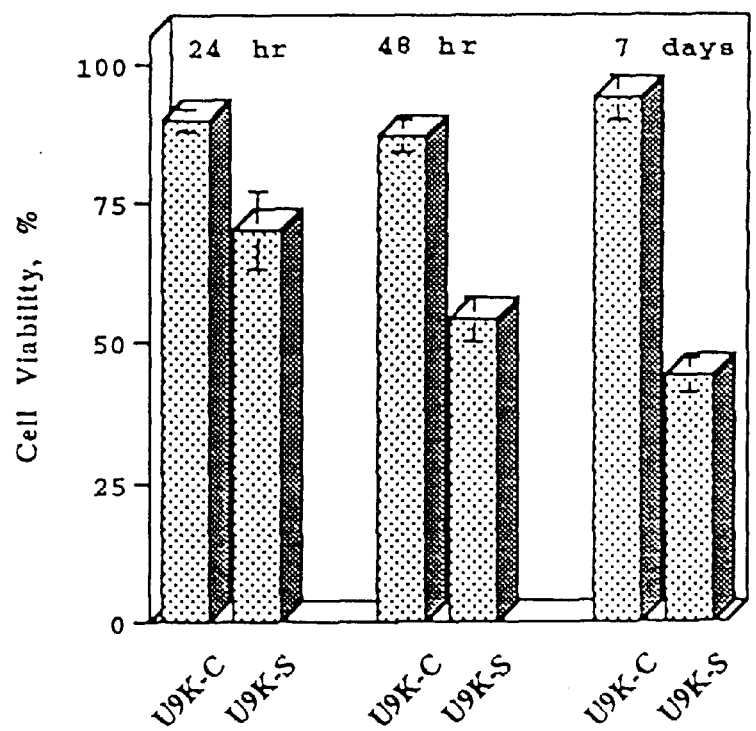
FIG. 5B presents a time course of cell viability post-TNF treatment. U9K-C and U9K-S cells were treated with 0.5 ng/ml of TNF over a time period of 7 days.
Figure 5C:
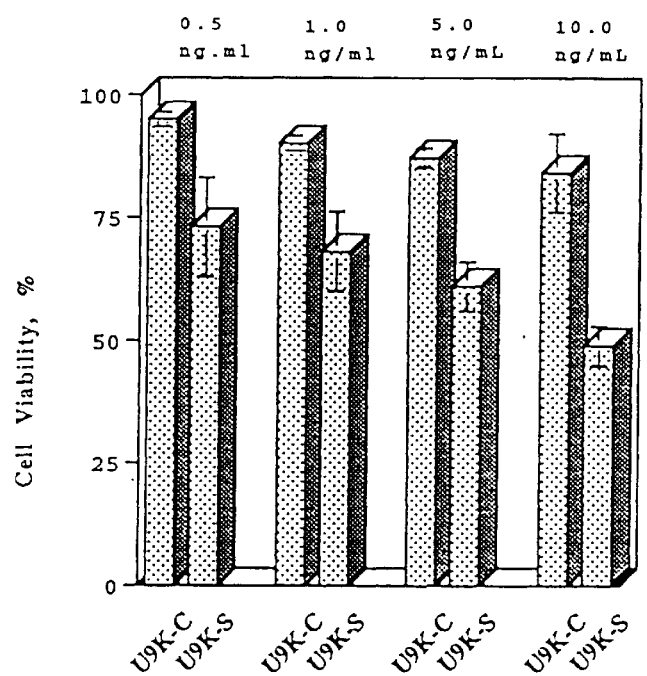
FIG. 5C presents a dose response of TNF effects on cell viability. U9K-C and U9K-S cells were treated with indicated concentrations of TNF-α (0.5 ng/ml to 10 ng/ml) for 24 hours.
Figure 5D:
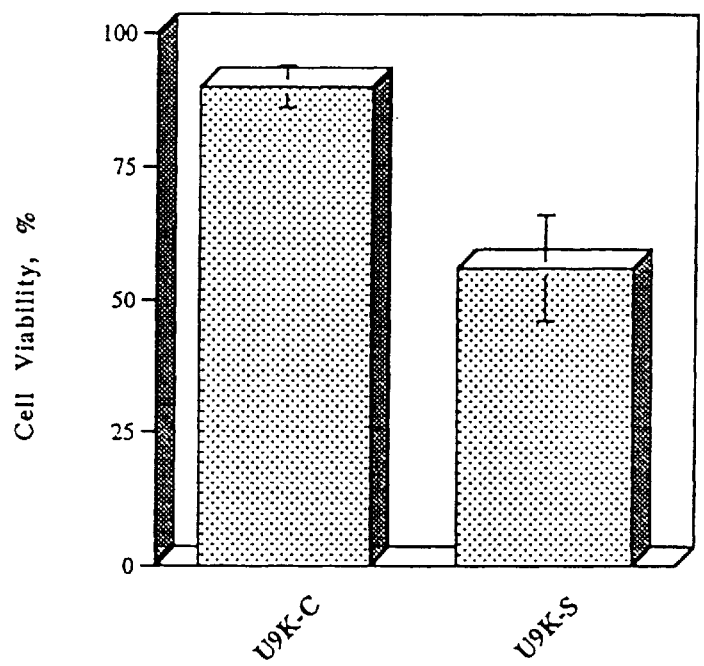
Figure 6:
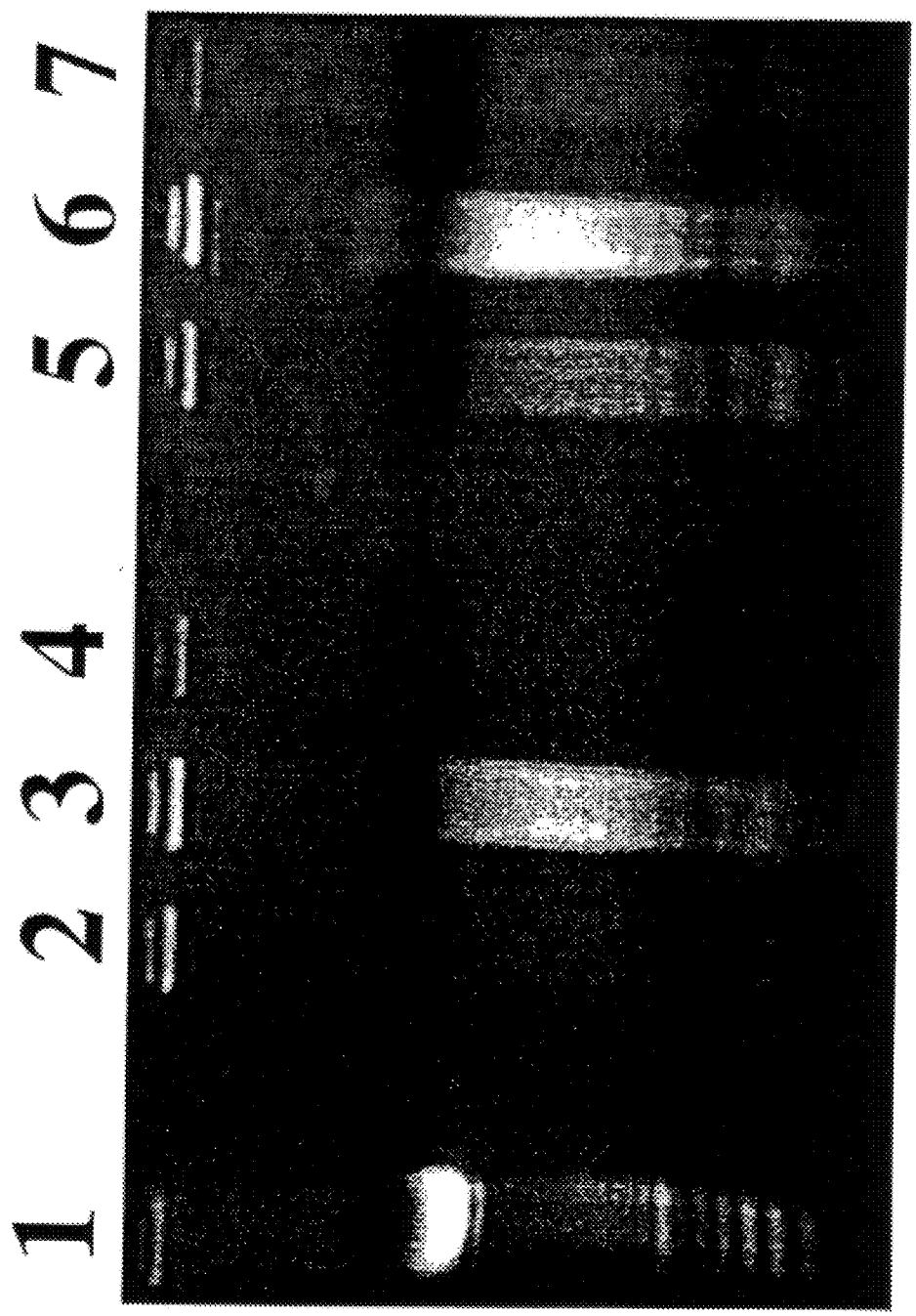
FIG. 6 shows an oligonucleosomal DNA ladder analysis of apoptosis in different U937 cells post TNF-α treatment. After the U937 subclones were treated with 0.5 ng/mL TNF-α for 18 hours, small molecular weight DNA was extracted by the method of Herrmann et al (1994) and was fractionated by 1% agarose gel electrophoresis. Lane 1 contains a 100 base-pair DNA marker; lanes 2 to 4 contain U9K-C, U9K-S and U9K-A cells with no TNF treatment, respectively; and lanes 5 to 7 contain TNF-α-treated U9K-C, U9K-S and U9K-A cells, respectively.

To further demonstrate the differential susceptibility of the three U937 subclones to TNF-α-induced cytotoxicity, cell viability was determined by trypan blue exclusion staining after the cells were treated for 18 hours with TNF-α. As expected, FIG. 5A1 illustrates that the viability of both U9K-C and U9K-A cells was not affected by TNF-α. However, a high level of expression of PKR predisposes the U9K-S cells to TNF-α cytotoxicity so that up to 25% and 50% of these cells were killed, in a dose-dependent manner, by TNF-α treatment for 18 hours at final concentrations of 0.5 and 5 ng/mL, respectively. The role of PKR in cell death was underscored by the observation that poly I:C, which activates PKR, killed up to 25% of the U9K-S cells over-expressing PKR after an 18 hour incubation with poly I:C at the low concentration of 0.1 μg/mL (FIG. 5A2). Again, both U9K-C and U9K-A cells were unaffected by poly I:C. As shown in FIG. 5B, prolonged treatment of U9K-S cells with TNF-α results in significant increases in cell death after 7 days (FIG. 5C). Additionally, higher concentrations of TNF-α induced a greater degree of cell death. A combination of TNF-α and poly I:C provides a cumulative effect on cancer cell killing. (FIG. 5D).

Incubation of parental cells as well as transformed cell clones with fetal bovine serum and culture medium did not result in the induction of TNF. In addition, transfection of the cell clones per se did not induce the expression of TNF activities as determined by bioassays and PCR assays.

Example 3

TNF-α-Induced Apoptosis Requires PKR.

To further confirm the role of PKR in TNF-α-induced apoptosis, small molecular weight DNA was isolated from the three U937 subclones after an 18 hour TNF-α treatment (0.5 ng/mL), using the ultra-sensitive extraction method of Herrmann et al., *Nucleic Acids Res* 22(24):5506–7 (1994)). Since a DNA ladder of 200 base pair multiples is a hallmark of apoptosis (Wyllie, A. H. et al., *Histochem J*, 13(4):681–92 (1981); Eamshaw, W. C., *Curr Opin Cell Biol*, 7(3):337–43 (1995)), FIG. 6 demonstrates that TNF-α effected apoptosis in U9K-C cells (compare lanes 2 and 5). Significantly, a deficiency in PKR rendered the U9K-A cells relatively protected from the apoptosis-inducing action of TNF-α (see lanes 4 and 7). Consistent with the results described in the previous examples, untreated PKR-overexpressing U9K-S cells exhibited spontaneous apoptosis (lane 3), which was further enhanced by TNF-α treatment (lane 6). The requirement of PKR for the TNF-α-induced apoptosis in U937 cells was corroborated by experiments in which the sensitivity of U9K-C cells to TNF-α was much ablated in the presence of a PKR-specific antisense oligonucleotide, but not a control oligonucleotide. The PKR-specific sense (control) and antisense oligonucleotides used in some experiments to inhibit apoptosis were 5' (SEQ ID NO:9) GAAGAAATGGCTG-
GTGATC 3' and (SEQ ID NO:10) 5' GATCACCAGC-
CATTTCTTC 3', respectively.

Example 4

TNF-α Induces RNA Degradation.

Figure 7:
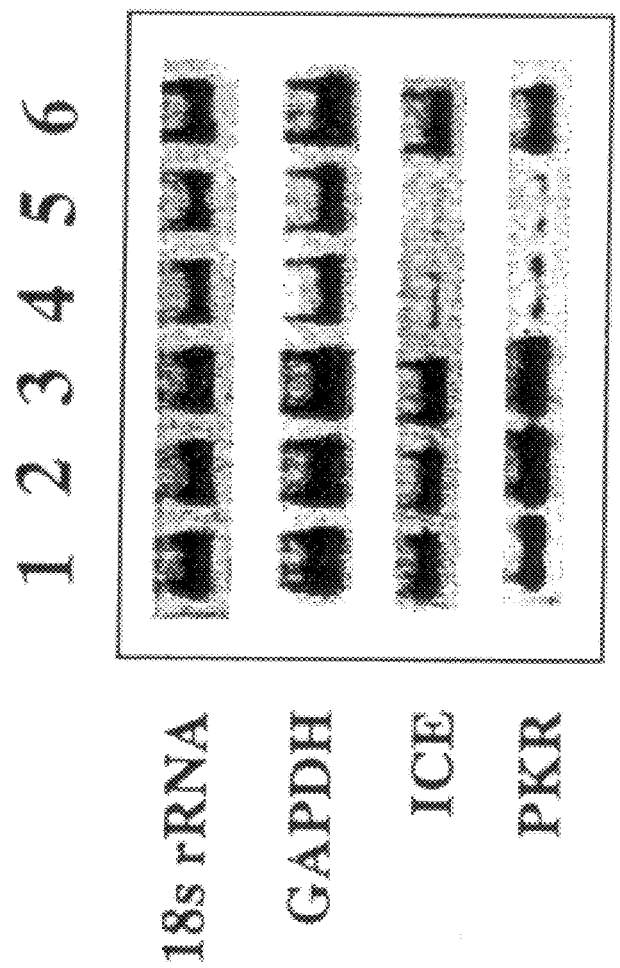
FIG. 7 shows that TNF-α induces RNA degradation in U937 cells. After the U937 subclones were treated with 0.5 ng/mL TNF-α for 18 hours, total RNA was extracted and was subjected to RT-PCR analysis for steady-state levels of various RNA species. Lanes 1 to 3 contain untreated U9K-C, U9K-S and U9K-A cells, respectively. Lanes 4 to 6 contain TNF-α-treated U9K-C, U9K-S and U9K-A cells, respectively. Levels of 18S ribosomal RNA and glyceraldehyde-3-phosphate dehydrogenase (GAPDH), corresponding to essential housekeeping genes, were measured. ICE, an interleukin-1 converting enzyme which is known to participate in apoptosis, was also measured.

To further elucidate the impact of TNF-α on U937 cells at the molecular level, steady-state levels of selective RNA species were studied by RT-PCR. For the essential, housekeeping genes of 18S ribosomal RNA and glyceraldehyde-3-phosphate dehydrogenase, the steady-state RNA levels were depressed in both U9K-C and U9K-S cells by about 50% after an 18 hour TNF-α treatment (0.5 ng/mL) (FIG. 7, lanes 4 and 5). Similarly, the steady-state mRNA levels were severely depressed by TNF-α in these cells for PKR and the interleukin-1β converting enzyme, which is known to participate in select apoptotic pathways (Kumar, S., *Trends Biochem Sci*, 20(5): 198–202 (1995)). Similar findings were obtained for other genes, including IFN-α and p53. In contrast, the steady-state levels of the various RNA species tested were not appreciably affected by TNF-α in all cases in U9K-A cells (FIG. 7, lanes 3 and 6).

Example 5

TNF-α induces PKR.

Figure 8A:
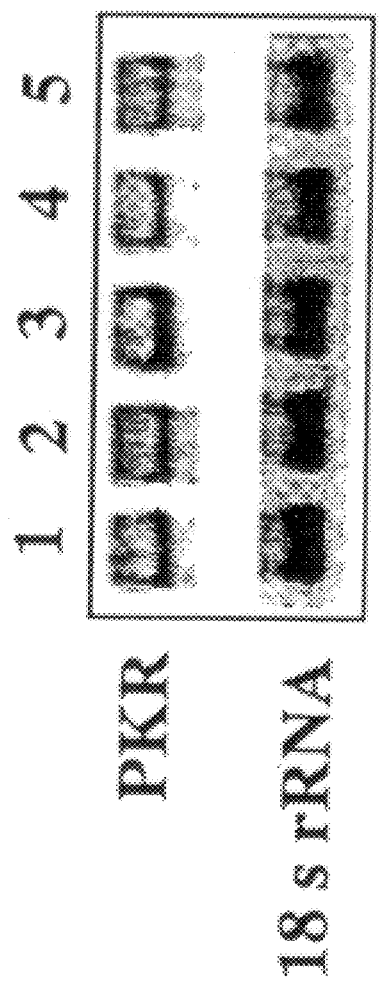
FIG. 8A shows that TNF-α upregulates the PKR gene. U9K-C cells were treated with 0.5 ng/mL TNF-α for indicated times. Total RNA was extracted and subjected to RT-PCR analysis for steady-state PKR and 18S rRNA mRNA levels; 18S rRNA messages served as PCR internal controls. Lanes 1 to 5 correspond to 0, 1, 2, 3 and 4 hours post addition of TNF-α.
Figure 8B:
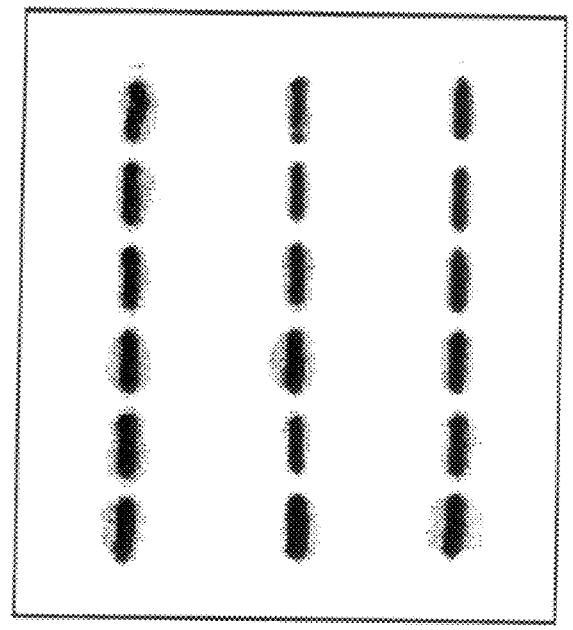
FIG. 8B further illustrates that TNF-α upregulates PKR protein synthesis. Total protein extracts from U937 cells treated with 0.5 ng/mL TNF-α were immunoblotted with anti-PKR (8B1) and anti-actin antibodies (8B2) using the ECL chemiluminescence system. Lanes 1–6 in both panels correspond to 0, 1, 2, 3, 4 and 6 hours post TNF-α treatment.
Figure 8B:
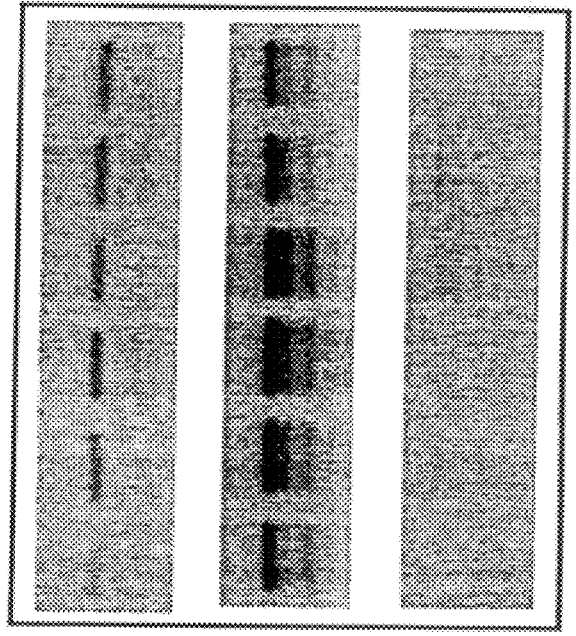

To investigate if TNF-α induces PKR as part of its apoptosis-promoting repertoire, steady-state PKR mRNA levels in U9K-C cells were monitored by RT-PCR during TNF-α treatment. Upon addition of TNF-α (0.5 ng/mL) to U9K-C cells, there was an early induction of PKR, as seen in FIG. 8A. This induction peaked at 2 hours post addition of TNF-α, but was down-regulated thereafter. Cytokine genes are very tightly-regulated. They are turned on transiently to minimize toxic effects. Once the gene and gene products are activated, transcription of the gene will be rapidly inactivated. This finding of TNF-induced expression of PKR was further demonstrated by Western blot analysis. As expected, U9K-S cells had the highest endogenous level of PKR proteins (FIG. 8B, left panel, lane 1). Upon TNF-α treatment, PKR protein synthesis was upregulated in both U9K-C and U9K-S cells. In contrast, U9K-A cells did not exhibit response to TNF treatment (FIG. 8B).

Example 6

PKR Expression in Stable Transfectants was Confirmed by Western Blot Analysis.

To further confirm PKR over-expression in the pCMV-PKR-transfected cell lines, Western blot analysis was performed using anti-PKR polyclonal antibodies specific for human PKR. Cell extracts (100 μg) were separated on a 10% SDS-polyacrylamide gel and electrotransferred onto a nitrocellulose membrane. The membranes were incubated with anti-PKR polyclonal antibodies (Meurs et al., *Cell*, (1990)) at 1:1000 in BLOTTO (5% nonfat dry milk, 0.05% Tween-20 in Tris-buffered saline). Final detection of PKR was facilitated by probing with a secondary horseradish peroxidase-conjugated goat anti-mouse antibody (Santa Cruz Biotech) and using a chemiluminescence Luminol method (Amersham USB). FIG. 2 demonstrates that U9K-S cells harboring the PKR suppression vector constitutively expressed higher levels of PKR mRNA and protein.

Example 7

TNF-α Has a Negative Effect on HeLa Cell Viability, But Not in Chang Liver Cells.

To further demonstrate the effects of PKR on tumor cell susceptibility to TNF-α-induced cytotoxicity, HeLa cells were transfected with the above plasmid constructs to generate different cell subclones. HeK-C represents HeLa cells transfected by the parental plasmid pRC-CMV without PKR inserts. HeK-S represents HeLa cells transfected with the plasmid containing PKR insert in the sense orientation. HeK-A represents HeLa cells transfected with the plasmid containing PKR insert in the antisense orientation. Cell viability was determined by trypan blue exclusion staining after the cells were treated for 18 hours with TNF-α. As expected, FIG. 9A illustrates that the viability of both HeK-C and HeK-A cells was not affected by TNF-α. In contrast, over-expression of PKR seemed to heighten the sensitivity of HeK-S cells to TNF-α-induced cytotoxicity (FIG. 9A), similar to the effects of TNF-α on U937 subclones seen in FIG. 5. Similarly, there were significant increases in HeLa cell death in a dose-dependent manner when HeK-S cells were treated with poly I:C (FIG. 9B). The effects of both poly I:C and TNF-α were heightened when combined treatments were performed. At least 80% of HeK-S cells died spontaneously with the combined low dose TNF-α (0.5 ng/ml) and poly I:C (0.1 μg/ml) treatment when compared to 30% cell death of HeK-C, underscoring the contribution of PKR in apoptosis (FIG. 9C). This further example illustrates that the effect of PKR in mediating TNF-induced programmed cell death appears to extend to tumor cell types of diverse origins, i.e., promonocytic leukemic as well as cervical carcinoma cells.

While PKR over-expression in transfected cancer cells (e.g., U937 and HeLa) results in increased propensity to apoptosis, this phenomenon was not observed in Chang liver cells. This is a non-malignant cell line established from human liver tissue and has been used for decades in human biology research. It is interesting to note PKR and TNF are effective in inducing apoptosis in cancer cells but not in non-malignant cells.

Example 8

PKR and TNF Kill Tumors in vivo.

Congenitally athymic nude mice (nu/nu; 6-week old females) were maintained in a pathogen-free environment throughout the experiments. They were injected with $4 \times 10^6$ HeLa cells in DMEM medium subcutaneously on the right side of the lower limb. The animals were observed for the growth of tumor over a 2–3 week period. Typically, tumors of 2 to 3 cm were seen in these mice upon injection with HeK-C cells (with endogenous wild type PKR). In contrast, the tumor mass was smaller for mice injected with HeK-S cells. The mice were then treated with varying doses of TNF-α (ranging between 0.1 μg to 10 μg/kg/day) for 5 days. Poly I:C was added to the TNF-α treatment at 0.1 to 10 mg/kg/day. The tumor size was diminished following poly I:C and TNF treatments.

This model can be used to assess the effects of other chemotherapeutic agents on PKR(+) tumor cells. These agents include cis-platinum and actinomycin D. Additionally, the above experiments can be performed with the use of parental HeLa cells injected into the nude mice. Following the formation of tumors, these mice are infected with viral vectors encoding the PKR gene and driven by an HPV-specific promoter including E6 or E7. The viral vector used can be any viral vector for infecting the animals. These include retroviral, adenovirus, or adeno-associated viral vectors. Due to the nature of the E6 or E7 promoter, the PKR gene will be expressed in HeLa cells, but not in other mouse tissues. Following this, the animals will be treated with TNF or other chemotherapeutic agents. They will be examined for the effects of these treatment protocols on their HeLa tumor size.

By increasing the level of PKR protein, and therefore PKR activity, in animal cells, the level of apoptosis was increased. Expression plasmids or select viral vectors encoding PKR can be used to transfect or infect animal cancer cells resulting in a higher constitutive or inducible level of PKR are useful for cancer therapy. The cells over-expressing PKR are very sensitive to low doses of TNF-α and poly I:C, and rapidly progress to apoptosis.

PUBLICATIONS

1. Orrenius, S., *J Intern Med*, 237:529–36 (1995).
2. Steller, H., *Science*, 267:1445–9 (1995).
3. Lee, S. B. & Esteban, M., *Virology*, 199:491–6 (1994).
4. Kirchhoff, S., Koromilas, A. E., Schaper, F., Grashoff, M., Sonenberg, N. & Hauser, H., *Oncogene*, 11:439–45 (1995).
5. Proud, C. G., *Trends Biochem Sci*, 20:241–6 (1995).
6. Jaramillo, M. L., Abraham, N. & Bell, J. C., *Cancer Invest*, 13:327–38 (1995).
7. Dever, T. E., Chen, J. J., Barber, G. N., Cigan, A. M., Feng, L., Donahue, T. F., London, I. M., Katze, M. G. & Hinnebusch, A. G., *Proc Natl Acad Sci U S A*, 90:461620 (1993).
8. Chong, K. L., Feng, L., Schappert, K., Meurs, E., Donahue, T. F., Friesen, J. D., Hovanessian, A. G. & Williams, B. R., *Embo J*, 11:1553–62 (1992).
9. Koromilas, A. E., Roy, S., Barber, G. N., Katze, M. G. & Sonenberg, N., *Science*, 257:1685–9 (1992).
10. Meurs, E. F., Galabru, J., Barber, G. N., Katze, M. G. & Hovanessian, A. G., *Proc Natl Acad Sci USA*, 90:232–6 (1993).
11. Der, S. D. & Lau, A. S., *Proc Natl Acad Sci USA*, 92:8841–8845 (1995).
12. Kumar, A., Haque, J., Lacoste, J., Hiscott, J. & Williams, B. R., *Proc Natl Acad Sci U S A*, 91:6288–92 (1994).
13. Tracey, K. J. & Cerami, A., *Annu Rev Med*, 45:491–503 (1994).
14. Beyaert, R. & Fiers, W., *Febs Lett*, 340:9–16 (1994).
15. Laster, S. M., Wood, J. G. & Gooding, L. R., *J Immunol*, 141:2629–34 (1988).
16. Grooten, J., Goossens, V., Vanhaesebroeck, B. & Fiers, W., *Cytokine*, 5:546–55 (1993).
17. Dressier, K. A., Matbias, S. & Kolesnick, R. N., *Science*, 255:1715–8 (1992).
18. Obeid, L. M., Linardic, C. M., Karolak, L. A. & Hannun, Y. A., *Science*, 259:1769–71 (1993).
19. Guy, G. R., Cao, X., Chua, S. P. & Tan, Y. H., *J Biol Chem*, 267:1846–52 (1992).
20. Van Lint, J., Agostinis, P., Vandevoorde, V., Haegeman, G., Fiers, W., Merlevede, W. & Vandenheede, J. R., *J Biol Chem*, 267:25916–21 (1992).
21. Herrmann, M., Lorenz, H. M., Voll, R., Grunke, M., Woith, W. & Kalden, J. R. *Nucleic Acids Res*, 22:5506–7 (1994).
22. Yeung, M. C., Pulliam, L. & Lau, A. S., *Aids*, 9:137–43 (1995).
23. Chomczynski, P. & Sacchi, N., *Anal Biochem*, 162:156–9 (1987).
24. Southern, E. M., *J Mol Biol*, 98:503–17 (1975).
25. Hu, Y. & Conway, T. W., *J Interferon Res*, 13:323–8 (1993).
26. Wyllie, A. H., Beattie, G. J. & Hargreaves, A. D., *Histochem J*, 13:681–92 (1981).
27. Earnshaw, W. C., *Curr Opin Cell Biol*, 7:337–43 (1995).
28. Kumar, S., *Trends Biochem Sci*, 20:198–202 (1995).
29. Leist, M., Gantner, F., Jilg, S. & Wendel, A., *J Immunol*, 154:1307–16 (1995).
30. Grell, M., Zimmermann, G., Hulser; D., Pfizenmaier, K. & Scheurich, P., *J Immunol*, 153:1963–72 (1994).
31. Wright, S. C., Kumar, P., Tam, A. W., Shen, N., Varma, M. & Larrick, J. W. *J Cell Biochem*, 48:344–55 (1992).
32. Barber, G. N., Wambach, M., Thompson, S., Jagus, R. & Katze, M. G., *Mol Cell Biol*, 15:3138–46 (1995).
33. Aronson, J. F., Herzog, N. K. & Jerrells, T. R., *Am J Trop Med Hyg*, 52:262–9 (1995).
34. Oyaizu, N., McCloskey, T. W., Than, S., Hu, R., Kalyanaraman, V. S. & Pahwa, S., *Blood*, 84:2622–31 (1994).
35. Merrill, J. E., Koyanagi, Y., Zack, J., Thomas, L., Martin, F. & Chen, I. S., *J Virol*, 66:2217–25 (1992). 36. Lau, A. S., Der, S. D., Read, S. E. & Williams, B. R., *Aids Res Hum Retroviruses*, 7:545–52 (1991).
37. Voth, R., Rossol, S., Klein, K., Hess, G., Schutt, K. H., Schröder, H. C., Meyer zum Buöschenfelde, K. H. & Muller, W. E., *J Immunol*, 144:970–5 (1990).
38. Lähdevirta, J., Maury, C. P., Teppo, A. M. & Repo, H., *Am J Med*, 85:289–91 (1988).
39. Wright, S.C., Jewett, A., Mitsuyasu, R. & Bonavida, B., *J Immunol*, 141:99–104 (1988).
40. Reddy, M. M., Sorrell, S. J., Lange, M. & Grieco, M. H., *J Acquir Immune Defic Syndr*, 1:436–40 (1988).
41. Suffys, P., Beyaert, R., De Valck, D., Vanhaesebroeck, B., Van Roy, F. & Fiers, W. *Eur J Biochem*, 195:465–75 (1991).
42. Schutze, S., Berkovic, D., Tomsing, O., Unger, C. & Kronke, M., *J Exp Med*, 174:975–88 (1991).
43. De Valck, D., Beyaert, R., Van Roy, F. & Fiers, W., *Eur J Biochem*, 212:491–7 (1993).
44. Watanabe, N., Yamauchi, N., Neda, H., Maeda, M., Tsuji, Y., Okamoto, T., Akiyama, S., Sasaki, H., Tsuji, N. & Niitsu, Y., *Jpn J Cancer Res*, 83:638–43 (1992).
45. Mestan, J., Brockhaus, M., Kirchner, H. & Jacobsen, H., *J Gen Virol*, 69:311320 (1988).
46. Nilsen, T. W., Maroney, P. A. & Baglioni, C., *J Virol*, 42:1039–45 (1982).
47. Vietor, I., Schwenger, P., Li, W., Schlessinger, J. & Vilcek, J., *J Biol Chem*, 268:18994–9 (1993).
48. Kim, M. Y., Linardic, C., Obeid, L. & Hannun, Y., *J Biol Chem*, 266:484–9 (1991).
49. Wiegmrann, K., Schutze, S., Machleidt, T., Witte, D. & Kronke, M., *Cell*, 78:1005–15 (1994).
50. Schutze, S., Potthoff, K., Machleidt, T., Berkovic, D., Wiegmann, K. & Kronke, M., *Cell*, 71:765–76 (1992).
51. Fujita, T., Reis, L. F., Watanabe, N., Kimura, Y., Taniguchi, T. & Vilcek, J., *Proc Natl Acad Sci USA*, 86:9936–40 (1989).
52. Tamura, T., Ishihara, M., Lamphier, M. S., Tanaka, N., Oishi, I., Aizawa, S., Matsuyama, T., Mak, T. W., Taki, S. & Taniguchi, T., *Nature*, 376:596–9 (1995).
53. Kamijo, R., Takeda, K., Nagumo, M. & Konno, K., *J Immunol*, 144:1311–6 (1990).
54. Bachem, M. G., Sell, K. M., Melchior, R., Kropf, J., Eller, T. & Gressner, A. M. *Virchows Arch B Cell Pathol Incl Mol Pathol*, 63:123–30 (1993).

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of identifying chemotherapeutic compounds comprising:
   introducing a nucleic acid encoding human PKR to at least one cancer cell with an expression system that expresses PKR in said cancer cell,
   contacting said cancer cell with at least one chemotherapeutic compound, and
   detecting a difference in said cancer cell exposed to said chemotherapeutic compound compared to a cancer cell not exposed to said chemotherapeutic compound,
   wherein said cancer cell is grown with or without serum and said chemotherapeutic compound is at a concentration of 1 µg/mL or less.

2. The method of claim 1, wherein said specific expression system comprises a vector.

3. The method of claim 2, wherein said vector is a viral vector derived from a virus selected from the group consisting of retrovirus, herpes simplex virus type I, adenovirus, adeno-associated virus, human papilloma virus (HPV), vaccinia, hepatitis B virus (HBV), and hepatitis delta virus (HDV).

4. The method of claim 1, wherein said expression system comprises a tissue-specific promoter.

5. The method of claim 4, wherein said tissue-specific promoter is selected from the group consisting of CEA, α-FP, E5 and E7.

6. The method of claim 1, wherein said expression system is a retrovirus.

7. The method of claim 4, wherein said expression system comprises an adenovirus, and said tissue-specific promoter is CEA and said concentration is 0.5 µg/mL or less.

8. The method of claim 7, wherein said cancer cell is a human colorectal cancer cell that further comprises at least 1×10⁹ human colorectal cancer cells.

9. The method of claim 7, wherein said human cancer cell is a human pancreatic cancer cell, and said human pancreatic cancer cell is exposed to human growth factors.

10. The method of claim 7, wherein said cancer cell is a human lung cancer cell.

11. The method of claim 4, wherein said expression system comprises a viral vector derived from an adeno-associated virus, and said tissue-specific promoter is CEA.

12. The method of claim 11, wherein said cancer cell is a human colorectal cancer cell that further comprises at least 1×10⁹ human colorectal cancer cells.

13. The method of claim 11, wherein said cancer cell is a human pancreatic cancer cell and said human pancreatic cancer cell is exposed to human growth factors.

14. The method of claim 11, wherein said cancer cell is a human lung cancer cell.

15. The method of claim 4, wherein said expression system is a hepatitis delta virus, and said tissue-specific promoter is α-FP.

16. The method of claim 15, wherein said cancer cell is a human hepatocarcinoma cell.

17. The method of claim 1, wherein said PKR increases the chemosensitivity of said cancer cell to recombinant TNF-α.

18. The method of claim 1, wherein said chemotherapeutic compound binds to a receptor inside said cancer cell.

19. The method of claim 1, wherein said chemotherapeutic compound binds to a receptor outside said cancer cell.

20. The method of claim 2, wherein said vector is a plasmid.

21. The method of claim 20, wherein said plasmid is selected from the group consisting of pRC/CMV, pcDNA3, pHBC, pHBS, pBPE5, and pHPE7.

22. The method of claim 21, wherein said plasmid is pRC/CMV and comprises a promoter from a gene selected from the group consisting of an HBV core antigen, an HBV suface antigen, an HPV E5 gene, and an HPV E7 gene.

23. The method of claim 3, wherein said virus is selected from the group consisting of HDV and HPV, wherein said HDV is a defective HDV and said HPV is a defective HPV.

24. The method of claim 1, wherein said chemotherapeutic compound is at a concentration of 0.5 µg/mL or less.

25. The method of claim 1, wherein said chemotherapeutic compound is at a concentration of 0.1 µg/mL or less.

26. The method of claim 1, wherein said chemotherapeutic compound is at a concentration of 10 ng/mL or less.

27. The method of claim 1, wherein said chemotherapeutic compound is at a concentration of 5 ng/mL or less.

28. The method of claim 1, wherein said chemotherapeutic compound is at a concentration of 0.5 ng/mL or less.

29. The method of claim 1, wherein said detecting step comprises observing said cancer cell for changes in cellular processes.

30. The method of claim 29, wherein said changes in cellular processes are changes in cell metabolism.

31. The method of claim 1, wherein said detecting step comprises observing said cancer cell for an indication of increased apoptosis.

32. The method of claim 1, wherein said detecting step comprises observing said cancer cell by a procedure selected from the group consisting of light microscopy, electron microscopy, analysis of DNA fragnents, and analysis of RNA levels.

33. The method of claim 1, wherein said detecting step comprises observing said cancer cell for a morphological or physiological change.

34. The method of claim 33, wherein said change is selected from the group consisting of new rounds of protein synthesis, cell shrinkage, cytoplasmic condensation, nuclear chromatin condensation, membrane blobbing, and DNA degradation into an oligonucleosomal ladder comprised of multiples of 200 base pairs.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Homo sapiens

<400> SEQUENCE: 1
caaaagggtc atcatctctg                                        20

<210> SEQ ID NO 2
<211> LENGTH: 20
<212> TYPE: DNA
<213> ORGANISM: Homo sapiens

<400> SEQUENCE: 2
cctgcttcac caccttcttg                                        20

<210> SEQ ID NO 3
<211> LENGTH: 20
<212> TYPE: DNA
<213> ORGANISM: Homo sapiens

<400> SEQUENCE: 3
ggcacccaga tttgaccttc                                        20

<210> SEQ ID NO 4
<211> LENGTH: 20
<212> TYPE: DNA
<213> ORGANISM: Homo sapiens

<400> SEQUENCE: 4
tccttgttcg ctttccatca                                        20

<210> SEQ ID NO 5
<211> LENGTH: 20
<212> TYPE: DNA
<213> ORGANISM: Homo sapiens

<400> SEQUENCE: 5
aatgctgcta caaaatctgg                                        20

<210> SEQ ID NO 6
<211> LENGTH: 20
<212> TYPE: DNA
<213> ORGANISM: Homo sapiens

<400> SEQUENCE: 6
atcatcctca aactcttctg                                        20

<210> SEQ ID NO 7
<211> LENGTH: 20
<212> TYPE: DNA
<213> ORGANISM: Homo sapiens

<400> SEQUENCE: 7
cgcagctagg aataatggaa                                        20

<210> SEQ ID NO 8
<211> LENGTH: 20
<212> TYPE: DNA
<213> ORGANISM: Homo sapiens

```
<400> SEQUENCE: 8
ttatgacccg cacttactgg                                              20

<210> SEQ ID NO 9
<211> LENGTH: 19
<212> TYPE: DNA
<213> ORGANISM: Homo sapiens

<400> SEQUENCE: 9
gaagaaatgg ctggtgatc                                               19

<210> SEQ ID NO 10
<211> LENGTH: 19
<212> TYPE: DNA
<213> ORGANISM: Homo sapiens

<400> SEQUENCE: 10
gatcaccagc catttcttc                                               19
```